(12) United States Patent
Ecklund et al.

(10) Patent No.: US 11,779,485 B2
(45) Date of Patent: *Oct. 10, 2023

(54) DEVICES AND SYSTEMS FOR URINE COLLECTION

(71) Applicant: Sage Products, LLC, Cary, IL (US)

(72) Inventors: Brian J. Ecklund, McHenry, IL (US); Kristin M. Sexton, Lake in the Hills, IL (US); Alex D. Kea, Chicago, IL (US); Daniel R. Ulreich, Cary, IL (US)

(73) Assignee: Sage Products LLC, Cary, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/986,051

(22) Filed: Nov. 14, 2022

(65) Prior Publication Data

US 2023/0062994 A1   Mar. 2, 2023

Related U.S. Application Data

(63) Continuation of application No. 17/128,480, filed on Dec. 21, 2020, now Pat. No. 11,523,933, which is a
(Continued)

(51) Int. Cl.
*A61F 5/453* (2006.01)
*A61F 5/443* (2006.01)

(52) U.S. Cl.
CPC .............. *A61F 5/453* (2013.01); *A61F 5/443* (2013.01)

(58) Field of Classification Search
CPC .................................. A61F 5/453; A61F 5/443
See application file for complete search history.

(56) References Cited

U.S. PATENT DOCUMENTS 3,881,486 A   5/1975  Fenton
4,020,843 A   5/1977  Kanall
(Continued)

FOREIGN PATENT DOCUMENTS

EP   0032138   7/1981
GB   1571657   7/1980
(Continued)

OTHER PUBLICATIONS

PCT Search Report and Written Opinion issued in PCT/US2019/018061 by the European Patent Office, dated May 10, 2019 (10 pages).

*Primary Examiner* — Catharine L Anderson
*Assistant Examiner* — Arjuna P Chatrathi
(74) *Attorney, Agent, or Firm* — McDonnell Boehnen Hulbert & Berghoff LLP

(57) ABSTRACT

A urine collection device includes a collection member extending from a proximal end to a distal end. The proximal end includes an opening that provides access to an internal cavity of the collection member. The internal cavity includes a first chamber in fluid communication with a second chamber. The urine collection device includes a spacer in the second chamber, a first attachment member extending from a bottom wall of the collection member at the proximal end, a second attachment member extending from a top wall of the collection member at the proximal end, and an outlet for egressing urine from the internal cavity of the collection member. The first attachment member defines an aperture. The collection member is suitable to (i) direct urine from the first chamber to the second chamber and (ii) direct the urine in the second chamber distally toward the outlet.

20 Claims, 35 Drawing Sheets

Related U.S. Application Data continuation of application No. 16/276,191, filed on Feb. 14, 2019, now Pat. No. 11,000,401.

(60) Provisional application No. 62/770,734, filed on Nov. 21, 2018, provisional application No. 62/735,686, filed on Sep. 24, 2018, provisional application No. 62/360,561, filed on Jul. 11, 2016.

(56) References Cited

U.S. PATENT DOCUMENTS

| | | | |
|---|---|---|---|
| 4,681,577 A | 7/1987 | Stern et al. | |
| 4,747,166 A | 5/1988 | Kuntz | |
| 4,790,834 A | 12/1988 | Austin | |
| 4,804,377 A | 2/1989 | Hanifl et al. | |
| 5,300,052 A | 4/1994 | Kubo | |
| 5,342,583 A | 8/1994 | Son | |
| 5,346,483 A | 9/1994 | Thaxton | |
| 5,735,837 A | 4/1998 | Ishikawa | |
| 6,464,674 B1 | 10/2002 | Palumbo et al. | |
| 6,508,794 B1 | 1/2003 | Palumbo | |
| 6,733,482 B1 | 5/2004 | Coles | |
| 10,226,376 B2 | 3/2019 | Sanchez | |
| 10,376,406 B2 | 8/2019 | Newton | |
| 10,376,407 B2 | 8/2019 | Newton | |
| 10,893,974 B2 | 1/2021 | Nyberg | |
| 11,523,933 B2 * | 12/2022 | Ecklund | A61F 5/443 |
| 2002/0193766 A1 | 12/2002 | Gell et al. | |
| 2003/0045843 A1 | 3/2003 | Kondo et al. | |
| 2003/0163120 A1 | 8/2003 | Harvie | |
| 2014/0182051 A1 | 7/2014 | Tanimoto et al. | |
| 2018/0028349 A1 | 2/2018 | Newton et al. | |
| 2019/0282391 A1 | 9/2019 | Johannes | |
| 2019/0365561 A1 | 12/2019 | Newton | |
| 2020/0390591 A1 | 12/2020 | Glithero | |

FOREIGN PATENT DOCUMENTS

| | | |
|---|---|---|
| GB | 2260907 | 5/1993 |
| WO | 2004/026194 | 4/2004 |
| WO | 2016/103242 | 6/2016 |

* cited by examiner

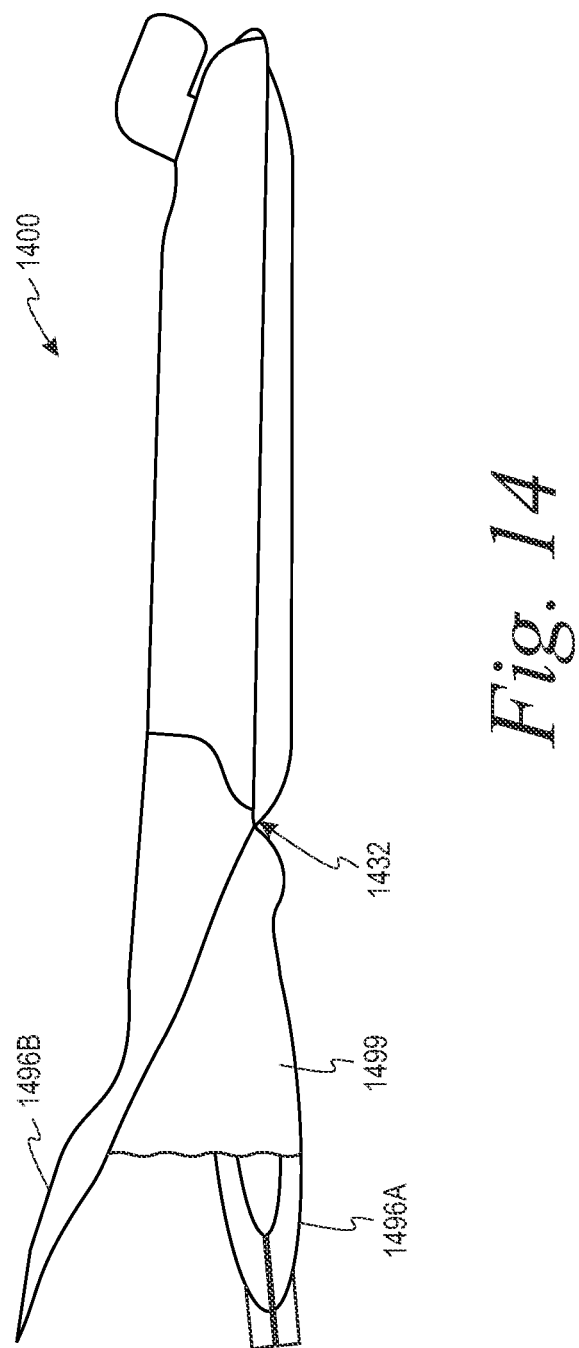

DEVICES AND SYSTEMS FOR URINE COLLECTION

CROSS-REFERENCE TO RELATED APPLICATIONS

The present disclosure is a continuation of U.S. application Ser. No. 17/128,480, filed Dec. 21, 2020, which is a continuation of U.S. application Ser. No. 16/276,191, filed Feb. 14, 2019 (now U.S. Pat. No. 11,000,401), which claims the benefit of priority of U.S. Provisional Application No. 62/630,561, filed Feb. 14, 2018, U.S. Provisional Application No. 62/735,686, filed Sep. 24, 2018, and U.S. Provisional Application No. 62/770,734, filed Nov. 21, 2018, the contents of which are all incorporated by reference in their entirety.

FIELD

The present disclosure generally relates to devices and systems for collecting urine discharged from the body of a user and carrying the urine away from the body.

BACKGROUND

Under various circumstances, a user may have limited or impaired mobility such that ordinary urinary functions and processes are rendered difficult (or impossible). For example, a person may have impaired mobility due to a disability or may be bedridden due to an injury or illness. In another example, a person may be subject to restricted occupational conditions under which the person has limited mobility. Also, for example, urine collection may be needed for monitoring purposes, such as for monitoring inputs and outputs in a clinical setting (e.g., in an intensive care unit, or for other clinical and/or laboratory testing).

Various approaches have been developed to address some of the problems or circumstances related to impaired or restricted urinary processes. However, prior approaches suffer from problems or limitations of their own. Internal urinary catheters, for example, can address problems arising from urinary incontinence or limited mobility, but urinary catheters can often be uncomfortable and can contribute to complications (for example, infections). Bed pans, as another example, are containers occasionally used for collecting urinary output of a bedridden person (such as a patient at a health care facility), but bed pans can contribute to patient discomfort, spillage, and issues related to sanitation or hygiene.

Other more recent approaches to urinary collection have been developed, which include a urine collection device configured to be placed external to, but in contact with the body for collecting and directing a fluid receptacle. However, the recent approaches also present challenges, such as in maintaining the placement of the device in appropriate contact with the body of a user, resulting in potential leakage and patient discomfort.

SUMMARY

In an example, a urine collection device for collecting urine includes a backing member and a collection member. The backing member includes a plurality of flexible members. Each flexible member extends from an outer portion of the backing member to an inner portion of the backing member. Each flexible member has a respective free end at the inner portion of the backing member. The respective free ends of the plurality of flexible members define an aperture in the backing member. The collection member is coupled to the backing member. The collection member is suitable to direct urine to an outlet of the collection member.

In another example, a system for collecting urine includes a urine collection device, a drain tube, a waste collection reservoir, and a vacuum device. The urine collection device includes a backing member and a collection member. The backing member includes a plurality of flexible members. One or more flexible members extend from an outer portion to an inner portion of the backing member. One or more flexible members have a respective free end at the inner portion of the backing member. The respective free ends of the plurality of flexible members define an aperture in the backing member.

The collection member is coupled to the backing member. The collection member is suitable to direct urine to an outlet of the collection member. The drain tube is coupled to the outlet of the collection member. The waste collection reservoir is coupled to the drain tube to receive the urine from the drain tube. The vacuum device can apply a vacuum pressure to the drain tube to assist in directing the urine from the outlet to the waste collection reservoir.

In another example, a urine collection device includes a backing member having a proximal side configured to contact a body of a user and a distal side opposite the proximal side. The backing member includes a plurality of flexible members. Each flexible member extends from an outer portion to an inner portion of the backing member. Each flexible member has a respective free end at the inner portion of the backing member. The backing member also includes an aperture defined by the respective free ends of the plurality of flexible members, and a layer of moisture wicking material for drawing urine discharged from the user to a collection portion of the backing member. The backing member further includes a vacuum tube at the collection portion of the backing member and distal of the layer of moisture wicking material. The vacuum tube includes an inlet for receiving the urine from the layer of moisture wicking material.

In another example, a urine collection device includes a collection member extending from a proximal end to a distal end. The proximal end includes an opening that provides access to an internal cavity of the collection member. The internal cavity comprises a first chamber in fluid communication with a second chamber. The urine collection device also includes a spacer in the second chamber, a first attachment member, a second attachment member, and an outlet. The first attachment member extends from a bottom wall of the collection member at the proximal end. The first attachment member also defines an aperture. The second attachment member extends from a top wall of the collection member at the proximal end. The outlet is suitable for egressing urine from the internal cavity of the collection member. The collection member is suitable to (i) direct urine from the first chamber to the second chamber and (ii) direct the urine in the second chamber distally toward the outlet.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

FIG. 14 illustrates a side view of a urine collection device, according to another example embodiment.

DETAILED DESCRIPTION

Figure 1A:
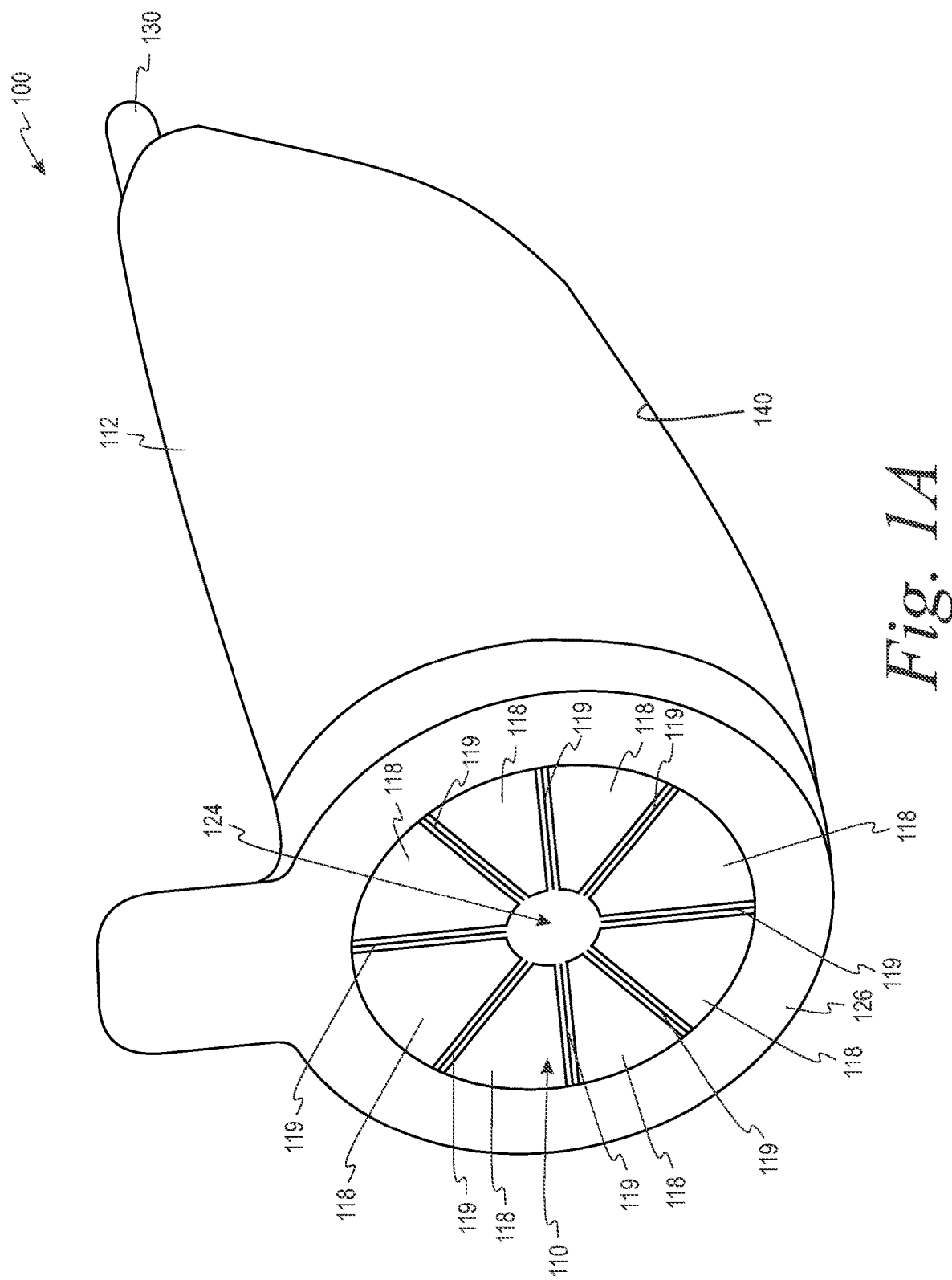
FIG. 1A illustrates a perspective view of a urine collection device, according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

As noted above, recent approaches to urinary collection have been developed, which include a urine collection device configured to be placed external to, but in contact with the body for collecting and directing a fluid receptacle. One such approach is a condom catheter. In general, a condom catheter is provided with an adhesive on an interior of the catheter. When the condom catheter is unrolled onto a user's penis, the adhesive is between the penis and the inner surface of the condom. In this way, the adhesive can adhere the condom directly to the penis. This approach can be uncomfortable for the user given that the adhesive is in contact with a relatively sensitive area of the body.

Additionally, a condom catheter may require a relatively snug fit with the penis. If the condom catheter is too tight, the user may experience discomfort. If the condom is too loose, it may not remain properly positioned on the penis of the user. This problem can be exacerbated by the fact that different users have differently sized penises. As such, it can be difficult to determine which size is appropriate for a given user. Moreover, the processes of attaching the condom catheter to the user and removing the condom catheter can be complicated and difficult for users and medical caregivers.

The devices and systems of the present disclosure provide for urine collection devices that can address at least some of the drawbacks of existing male external catheters. Within examples, a urine collection device includes a backing member coupled to a collection member. The backing member has a proximal side for contacting a pelvic area of a user and a distal side facing the collection member. The collection member is coupled to the backing member at a proximal end of the collection member and has an outlet for coupling to a drain tube at a distal end of the collection member. In general, the collection member is suitable to divert urine discharged from the body of the user to the outlet.

The backing member includes a plurality of flexible members, which define an aperture. When a penis is inserted through the aperture, the flexible members deflect toward the collection member, which expands the size of the aperture according to the size of the penis. While the penis is inserted through the aperture in the backing member, the flexible members apply a force on the penis that assists in retaining the penis in a desired position relative to the urine collection device. As the size of the aperture can expand to an extent commensurate with the size of the particular user's penis, the backing member can provide a more universal fit for a relatively broad range of the male population.

Additionally, in some examples, the backing member can include an adhesive on the proximal side. In this arrangement, when the urine collection device is attached to a user, the adhesive can contact and adhere to a pelvic area of the user to assist in retaining the urine collection device in the desired position. By providing the adhesive on the proximal side, which contacts the pelvic area of the user, the adhesive can more comfortably adhere the urine collection device to a less sensitive part of the body than a condom catheter.

Also, within examples, the collection member can have a size and shape that is adapted to loosely envelope the penis of the user. This can provide for improved comfort relative to condom catheters, which require a more snug fit to be retained on the penis. The collection member can be arranged to loosely envelope the penis, at least in part, because of the features of the backing member that assist in retaining the urine collection device on (or in a particular position with respect to) the penis Among other benefits, the urine collection devices described herein are easy to securely attach and can keep the skin relatively dry (i.e., with relatively little contact with urine). This can help to reduce (or prevent) skin breakdown and/or infection.

In additional or alternative examples, a urine collection device includes a collection member extending from a proximal end to a distal end. The proximal end includes an opening that provides access to an internal cavity of the collection member. The internal cavity comprises a first chamber in communication (i.e., fluid communication) with a second chamber. In use, a user's penis can be received through the opening in the first chamber and the penis can be separated from the second chamber by an inner wall. Additionally, the second chamber can include a spacer that assists in maintaining the penis in an elevated position above a bottom wall of the collection member.

The urine collection device can be secured to the user by a first attachment member and a second attachment member. For example, the first attachment member can define an aperture and a plurality of flexible members, which are movable relative to each other to expand and/or reduce a size of the aperture. In use, the flexible members can be manipulated to expand the aperture to facilitate positioning the penis in the aperture, and then the flexible members can be manipulated to reduce the aperture to an appropriate size that is commensurate with the particular size and shape of the penis. The first attachment member can then be secured to the pelvic area of the user (e.g., via an adhesive and/or a tape).

The second attachment member can extend from a top wall of the collection member at the proximal end. In use, the second attachment member can be secured to the pelvic area of the user above the first attachment member such that the penis extends through the aperture, above the first attachment member, below the second attachment member, and into the first chamber of the collection member.

When the user urinates with the urine collection device secured to the user in this manner, the urine is initially received in the first chamber. The collection member then directs the urine from the first chamber to the second chamber (e.g., via a plurality of perforations in the inner wall separating the first chamber and the second chamber). The collection member further directs the urine in the second chamber distally toward an outlet that is suitable for egressing the urine from the internal cavity of the collection member.

Thus, within examples, the urine collection device can reduce (or minimize) contact between the user's penis and the urine the urine collection device 1000, thereby improving sanitary conditions, reducing the risk of infection, and/or improving user comfort. Additionally, the arrangement of the attachment members and the collection member can provide a more universal fit for a relatively broad range of the male population by securing the urine collection device to the user via a dynamically adjustable aperture proximal of a relatively large opening in the collection member.

Figure 1B:
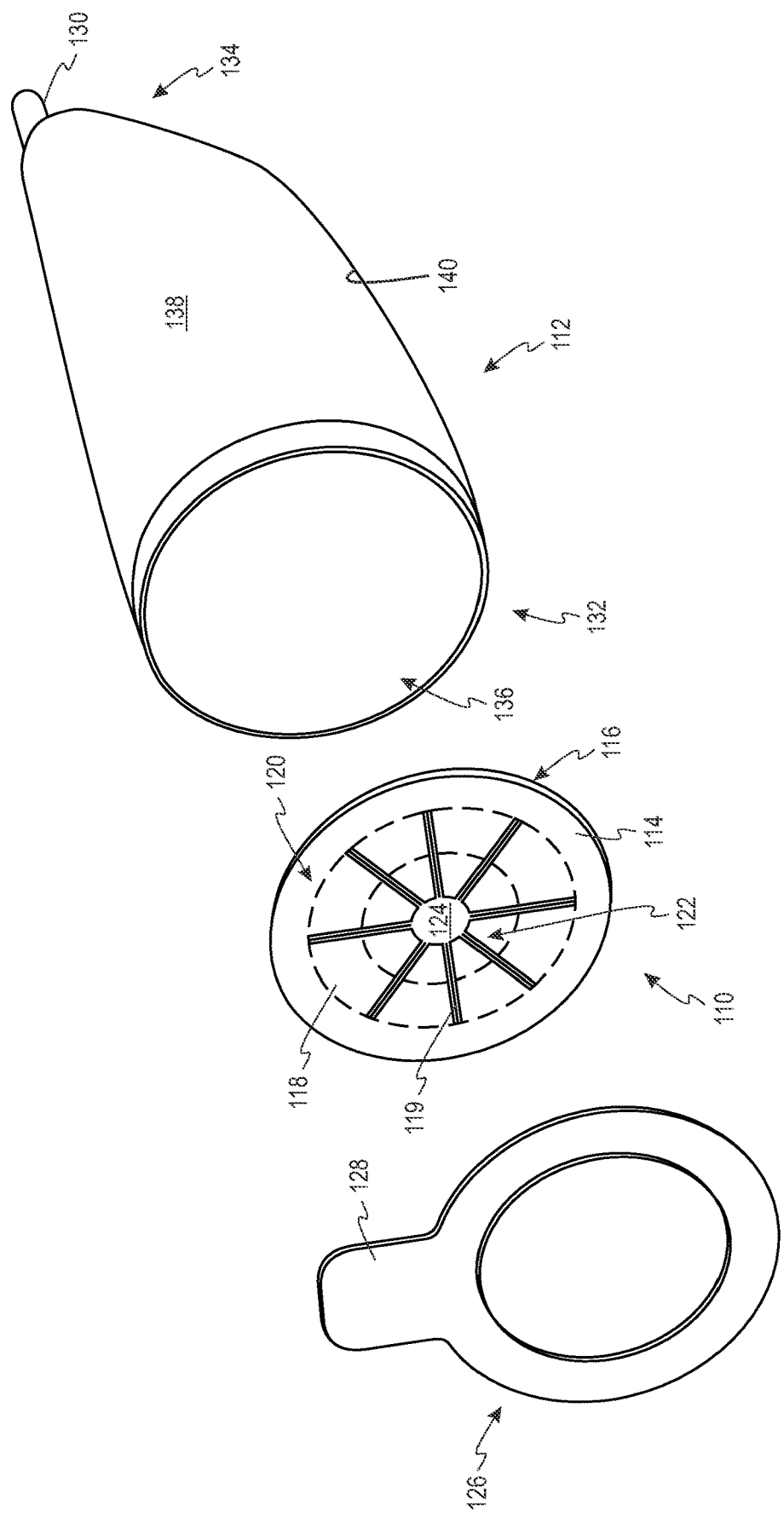
FIG. 1B illustrates an exploded view of the urine collection device of FIG. 1A, according to an example embodiment.

Referring to FIG. 1A-1B, a urine collection device 100 is depicted according to an example embodiment. More specifically, FIG. 1A depicts a perspective view of the urine collection device 100 and FIG. 1B depicts an exploded view of the urine collection device 100.

As shown in FIGS. 1A-1B, the urine collection device 100 includes a backing member 110 coupled to a collection member 112. The backing member 110 has a proximal side 114, which is suitable for contacting a pelvic area of a user when the urine collection device 100 is attached to the user. Additionally, the backing member 110 has a distal side 116, which opposes the proximal side 114 and faces the collection member 112.

The backing member 110 includes a plurality of flexible members 118, which each extend from an outer portion 120 of the backing member 110 to an inner portion 122 of the backing member 110. Additionally, each flexible member 118 has a respective free end at the inner portion 122 of the backing member 110.

As shown in FIGS. 1A-1B, the respective free ends of the flexible members 118 define an aperture 124 in the backing member 110. In FIGS. 1A-1B, the aperture 124 is circular. However, in other examples, the aperture 124 can have a different shape such as, for instance, an oval shape, a star shape, an octagon shape, a hexagon shape, another polygonal shape, and/or a non-polygonal shape.

In FIGS. 1A-1B, the flexible members 118 extend radially between the aperture 124 and the outer portion 120 of the backing member 110. More specifically, the flexible members 118 are defined laterally by a plurality radially-directed slits 119 in the proximal side 114 and the distal side 116 of the backing member 110. In this arrangement, the flexible members 118 are non-overlapping relative to each other, and are generally tapering in shape. As described in further detail below, the flexible members 118 can at least partially overlap each other and/or have different shapes in alternative examples.

In some examples, prior to attachment to a user, the flexible members 118 can be generally coplanar with each other. For instance, as shown in FIGS. 1A-1B, the flexible members 118 can be positioned such that the proximal side 114 and the distal side 116 of the backing member 110 each provide a substantially flat surface, which define a plane of the backing member 110. Additionally, in this initial state prior to attachment to the user, the aperture 124 has an initial size.

Within examples, the flexible members 118 are suitable to deflect distally toward the collection member 112 to expand the size of the aperture 124. Specifically, the flexible members 118 can deflect obliquely to the plane of the backing member 110 responsive to the user inserting a penis through the aperture 124. The extent to which the flexible members 118 deflect is related to a size of the penis inserted through the aperture 124. As such, the flexible members 118 can dynamically flex thereby expanding the aperture 124 to accommodate a specific size and/or shape of a user's penis.

While the penis is inserted through the aperture 124, the flexible members 118 apply a force on the penis that assists in retaining the penis in a desired position relative to the urine collection device 100. As the size of the aperture 124 can expand to an extent commensurate with the size of the particular user's penis, the backing member 110 can provide a more universal fit for a relatively broad range of the male population.

Within examples, the proximal side 114 of the backing member 110 can include an adhesive 126 to assist in attaching the backing member 110 to the user. For instance, in some implementations, the adhesive 126 can be coupled to the outer portion 120 of the proximal side 114 of the backing member 110. By coupling the adhesive 126 to outer portion 120, the backing member 110 can be attached to the pelvic area of the user with relatively little (or minimal) impact on the deflection of the flexible members 118. Further, because the adhesive 126 is arranged to attach to the pelvic area instead of the user's penis, the adhesive 126 can adhere the urine collection device 100 to a less sensitive area of the user's body than other catheters, which provide adhesive for contacting a substantial portion of the shaft of the penis.

As shown in FIG. 1, the adhesive 126 can extend around the entire outer portion 120 in some examples. This can facilitate providing a seal around the penis of the user and, thus, reduce (or prevent) leakage of urine from the urine collection device 100. However, in other examples, the adhesive 126 can be coupled to one or more sections of the outer portion 120 as opposed to the entire outer portion 120.

Optionally, to increase the surface area of the adhesive 126 and, thus, the surface area of attachment between the urine collection device 100 and the user, the adhesive 126 can be additionally or alternatively coupled to an anchor tab 128, which extends outwardly away from the outer portion 120 of the backing member 110. Although the urine collection device 100 shown in FIGS. 1A-1B includes a single anchor tab 128, the urine collection device 100 can have more than one anchor tab 128 in other examples.

Additionally or alternatively, the adhesive 126 can be coupled to the proximal side 114 of the flexible members 118. In this way, the adhesive 126 can facilitate adhering the urine collection device 100 to a base of the penis of the user in addition or alternative to the pelvic area of the user.

The collection member 112 is suitable to direct urine to an outlet 130 of the collection member 112. As shown in FIGS. 1A-1B, the collection member 112 extends from a proximal end 132 to a distal end 134. The proximal end 132 includes an opening 136 aligned with the aperture 124 of the backing member 110 such that a combination of the aperture 124 and the opening 136 provides access to an internal cavity 138 of the collection member 112. As such, when the user inserts the penis through the aperture 124, the penis also extends through the opening 136 and is received in the internal cavity 138.

The internal cavity 138 can be defined by an inner surface 140 of the collection member 112. Within examples, the collection member 112 can have a size and shape that provides for the inner surface 140 of the collection member 112 loosely enveloping the penis. For instance, in one implementation, at least a portion of an inner surface 140 of the collection member has a circumference, which is greater than a circumference of the aperture 124 of the backing member 110. By loosely enveloping the penis, the collection member 112 can reduce (or minimize) discomfort of the user relative to condom catheters, for example.

As noted above, the collection member 112 is suitable to direct urine to the outlet 130. For instance, the collection member 112 can be made from a fluid impermeable material. As examples, the collection member 112 can be made from silicone, rubber, latex, and/or a thermoplastic. Additionally, in some examples, the collection member 112 can have a shape, which generally tapers inwardly over a portion of the collection member 112 along a direction from the opening 136 at the proximal end 132 toward the outlet 130 at the distal end 134.

Figure 2:
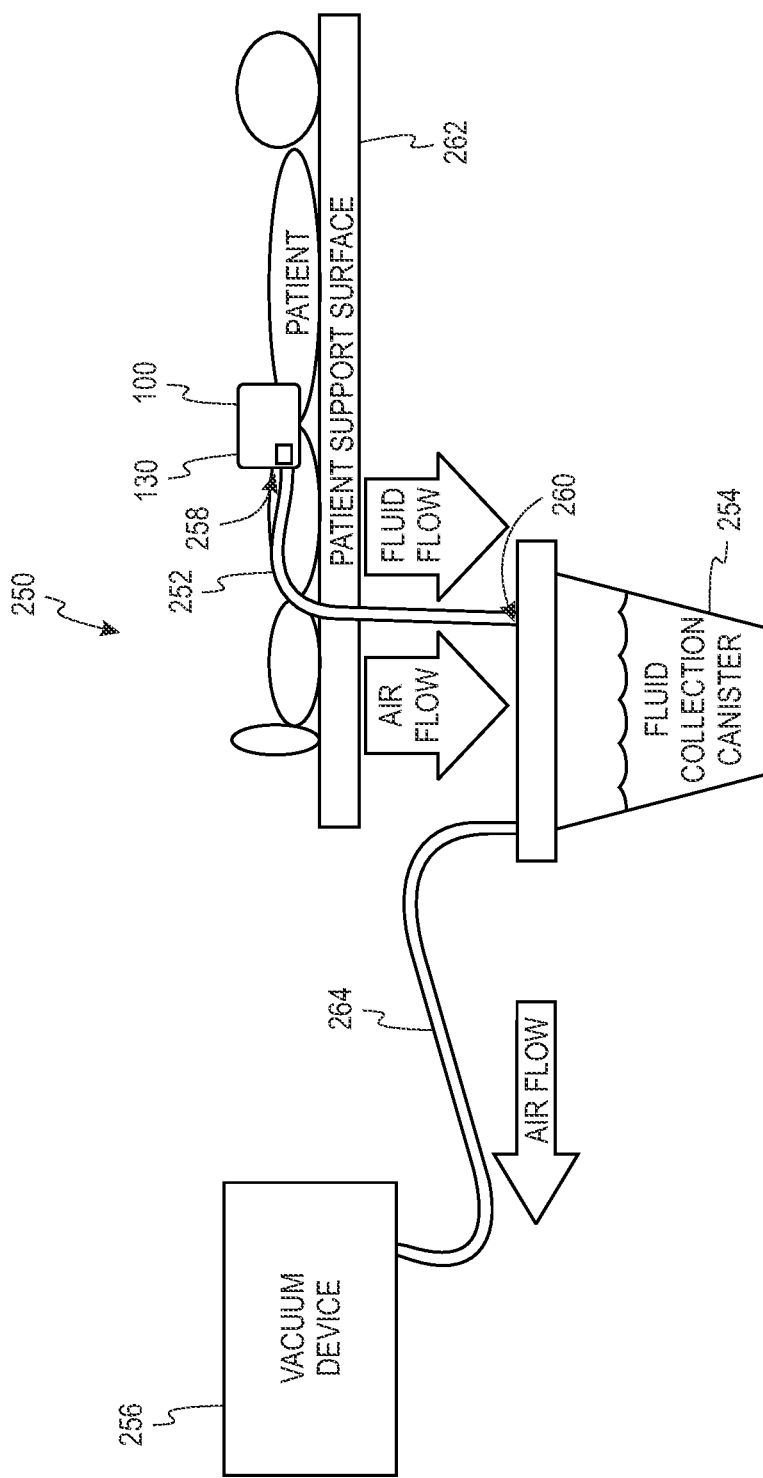
FIG. 2 illustrates simplified diagram of a system for collecting urine, according to an example embodiment.

The outlet 130 is suitable to be coupled to a drain tube (e.g., a drain tube 252 shown in FIG. 2). In some examples, the outlet 130 can include a thread for threadably coupling with the drain tube. In another example, the outlet 130 can include a hose barb and/or a Luer lock for coupling with the drain tube.

In the example of FIGS. 1A-1B, the flexible members 118 define the aperture 124 both (i) prior to being flexed and deflected towards the collection member 112 (i.e., prior to insertion of the penis through the backing member 110) and (ii) while being flexed and deflected towards the collection member 112 (i.e., when the penis is inserted through the backing member 110). In another example, the flexible members 118 can overlap such that the aperture 124 is formed only when the flexible members 118 are flexed and deflected obliquely to the plane of the backing member 110 (e.g., the aperture 124 is not formed when the flexible members 118 are arranged in the plane of the backing member 110). In that example, inserting the penis through the backing member 110 can cause the flexible members 118 to flex and deflect, and thereby form the aperture 124.

Referring now to FIG. 2, a simplified diagram of a system 250 for collecting urine is depicted according to an example embodiment. As shown in FIG. 2, the system 250 includes the urine collection device 100 described above. Additionally, the system 250 includes a drain tube 252, a waste collection reservoir 254, and a vacuum device 256.

A first end 258 of the drain tube 252 is coupled to the outlet 130 of the collection member 112. For example, the drain tube 252 can include a thread, a Luer lock, and/or other feature for coupling the drain tube 252 to the outlet 130. Within examples, the drain tube 252 can be a flexible material to facilitate directing the drain tube away from the user's body. It can be beneficial to direct the drain tube 252 away from the user's body (e.g., off the side of a bed) to reduce (or prevent) the drain tube 252 from accidental pulling and leakage resulting from such pulling.

The waste collection reservoir 254 is coupled to a second end 260 of the drain tube 252 to receive the urine from the drain tube 252. In one example, the waste collection reservoir 254 can be a leg bag, a drainage bag, or other container. In another example, the waste collection reservoir 254 can include a hanger and/or another structure for coupling the waste collection reservoir 254 to a patient support surface 262 (e.g., a bed and/or a wheelchair) used by the patient.

In some examples, the waste collection reservoir 254 can be a sealed container. This can, for example, reduce (or minimize) a risk of spillage and/or contamination. In some examples, the waste collection reservoir 254 can be disposable. In other examples, the waste collection reservoir 254 can be reusable. For instance, the waste collection reservoir 254 can be configured to be sterilized after a use and reused.

The vacuum device 256 can apply a vacuum pressure to the drain tube 252 to assist in directing the urine from the outlet 130 to the waste collection reservoir 254. For instance, the vacuum device 256 can include an air pump or other vacuum source, which is coupled to the waste collection reservoir 254 by an air tube 264. In one example, the air tube 264 can also be made of a flexible material.

In some examples, the vacuum device 256 can be a wall vacuum integrated into a room of a medical facility. In other examples, the vacuum device 256 can be integrated with the patient support surface 262. For instance, the vacuum device 256 can be integrated with a bed in a medical facility.

Within some examples, the system can also include an occlusion clip for selectively controlling the flow of urine in the drain tube. For instance, the occlusion clip can provide for stopping the flow of urine in the drain tube to facilitate changing and/or emptying the waste collection reservoir.

In use, the urine collection device 100 can be attached to the user. First, the urine collection device 100 can be positioned to align the aperture 124 with a head of a penis of the user. Next, the urine collection device 100 can be moved proximally towards the user to insert the penis through the aperture 124. As the penis is inserted through the aperture 124, the flexible members 118 deflect distally, which expands the size of the aperture 124 according to the size and shape of a portion of the penis in contact with the flexible members 118. The urine collection device 100 can be moved further proximally until the adhesive 126 contacts and attaches to a pelvic area of the user. In this position, the flexible members 118 can apply a retention force on the penis to assist in retaining the penis in the collection member 112 and the urine collection device 100 in a desired position on the user.

The drain tube 252 can be coupled to the outlet 130 at the first end 258 and the waste collection reservoir 254 at the second end 260. The vacuum device 256 can also be connected to the waste collection reservoir 254 by the air tube 264. The vacuum device 256 can then be operated to apply the vacuum pressure at the outlet 130 (e.g., via the air tube 264, the waste collection reservoir 254, and the drain tube 252).

As described above, the urine collection device 100 can beneficially be attached to users having penises of various sizes and/or shapes. However, in some instances, a user may have a condition, which is known as a "retracted penis". In such instances, a user's penis may not extend through the aperture 124 and/or the user's penis may extend only slightly through the aperture 124 such that urine discharged by the user may contact the backing member 110. In additional or alternative examples, the urine collection device 100 can include a backing member 110 that is adapted to divert discharged urine away from the user when the urine contacts the backing member 110.

Figure 8A:
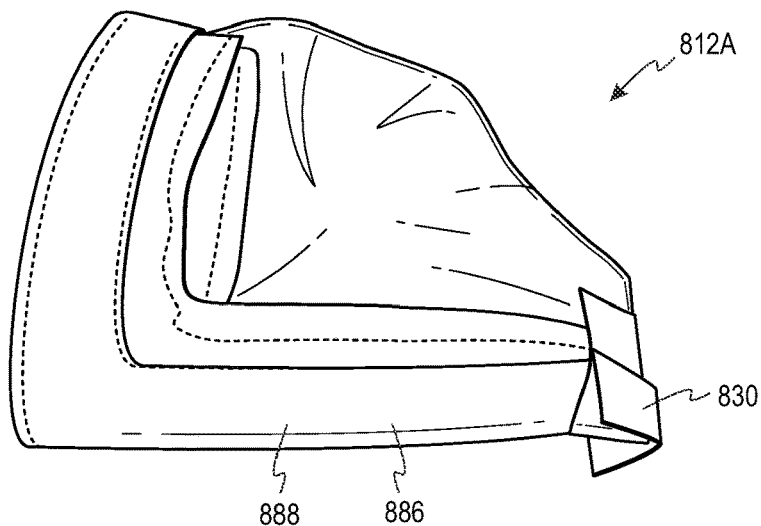
FIG. 8A illustrates a perspective view of a collection member, according to example embodiment.
Figure 8B:
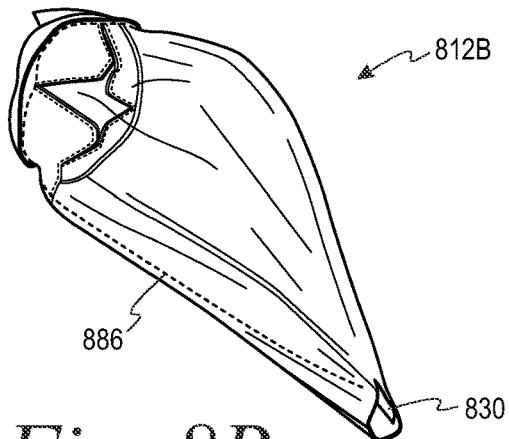
FIG. 8B illustrates a perspective view of a collection member, according to example embodiment.
Figure 8C:
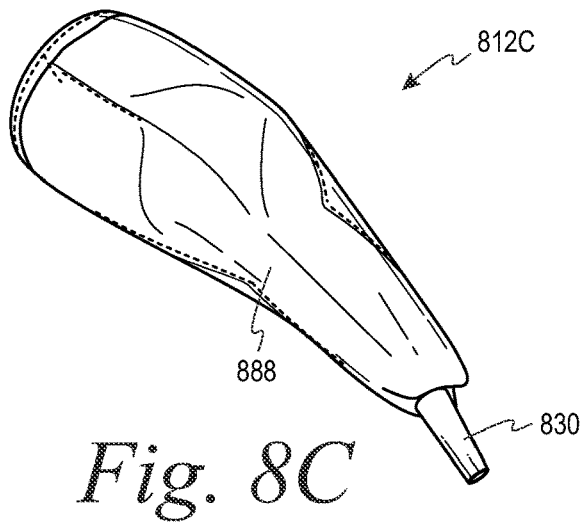
FIG. 8C illustrates a perspective view of a collection member, according to example embodiment.

FIGS. 3A-3D depict a backing member 310, which is adapted to divert discharged urine way from the user, according to another example embodiment. The backing member 310 can be used in connection with any of the components of the urine collection device 100 and/or the system 250 described above for FIGS. 1A-2. For instance, the backing member 310 can be coupled to a collection member such as, for instance, the collection member 112 described above (or any of the collection members 812A-812C described below with respect to FIGS. 8A-8C).

Figure 3A:
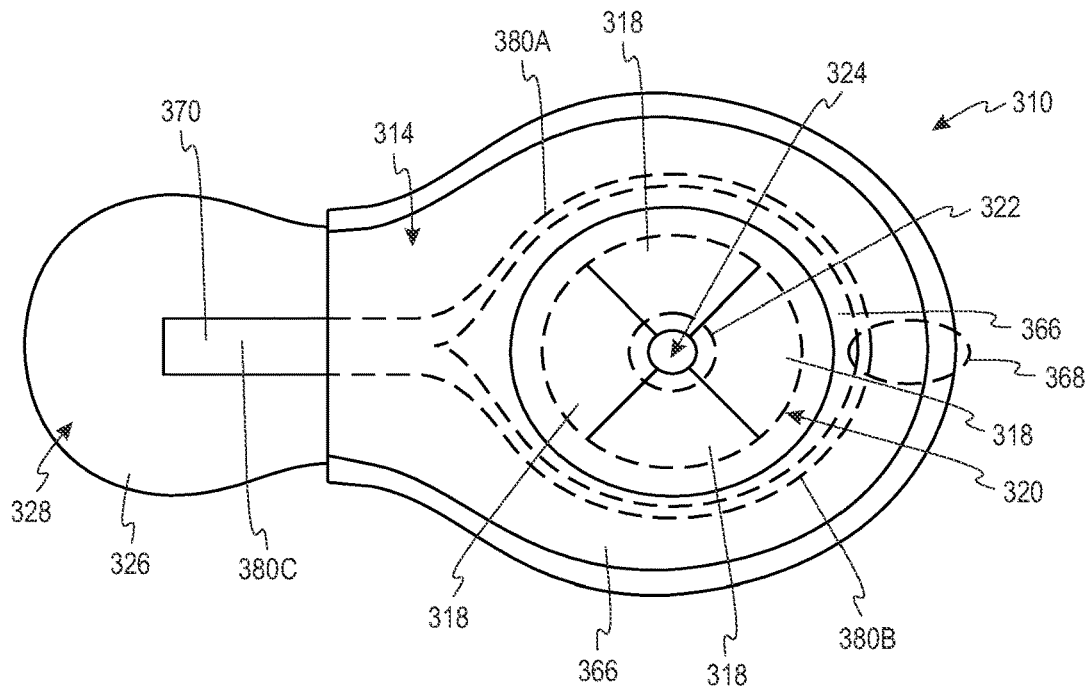
FIG. 3A illustrates a proximal side of a backing member, according to an example embodiment.
Figure 3B:
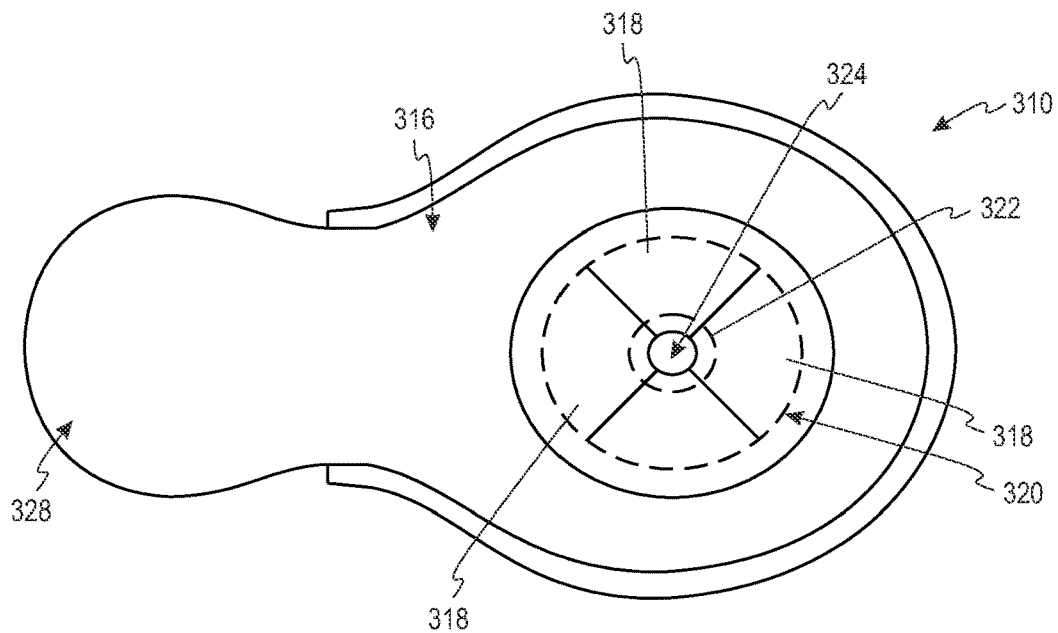
FIG. 3B illustrates a distal side of the backing member shown in FIG. 3A, according to an example embodiment.

As shown in FIGS. 3A and 3B, the backing member 310 has a proximal side 314 for contacting a body of a user, and a distal side 316 opposite the proximal side 314. The backing member 310 includes a plurality of flexible members 318. As described above, each flexible member 318 extends from an outer portion 320 to an inner portion 322 of the backing member 310. Also, each flexible member 318 has a respective free end at the inner portion 322 of the backing member 310.

Additionally, as shown in FIGS. 3A and 3B, the backing member 310 includes an aperture 324 defined by the respective free ends of the flexible members 318. As described above, the flexible members 318 can deflect in a direction from the proximal side 314 to the distal side 316 to expand a size of the aperture 324.

The backing member 310 further includes a layer of moisture wicking material 366 for drawing urine discharged from the user to a collection portion 368 of the backing member 310. The layer of moisture wicking material 366 can thus facilitate evacuating the discharged urine away from the body (e.g., by wicking and/or capillary effect). In this way, the layer(s) are less likely to feel wet to the user or cause dampness on the user's skin, improving comfort. Additionally, drawing urine away from the urethral opening of the user assists with inhibiting (or preventing) urine from leaking or flowing into a surrounding environment (e.g., a bed, a chair, or a wheelchair).

Within examples, the layer of moisture wicking material 366 can have a relative high absorptive rate, adsorption rate, and/or permeation rate such that the urine can be rapidly wicked and diverted to the collection portion 368 of the backing member 310. As one example, the layer of moisture wicking material 366 can include a polyester and/or spandex.

In some examples, the collection portion 368 can be a portion of the backing member 310 that is at lower (or the lowest elevation) when the backing member 310 is attached to the user. This can, for instance, allow gravity to assist the layer of moisture wicking material 366 in drawing the urine toward the collection portion 368.

The backing member 310 further includes a vacuum tube 370 at the collection portion 368 and distal of the layer of moisture wicking material 366. As shown in FIG. 3D, the vacuum tube 370 includes an inlet 372 for receiving the urine from the layer of moisture wicking material 366. In one example, the inlet 372 can be a notch in the vacuum tube 370 (i.e., a relatively small opening or aperture in the vacuum tube 370).

Figure 3C:
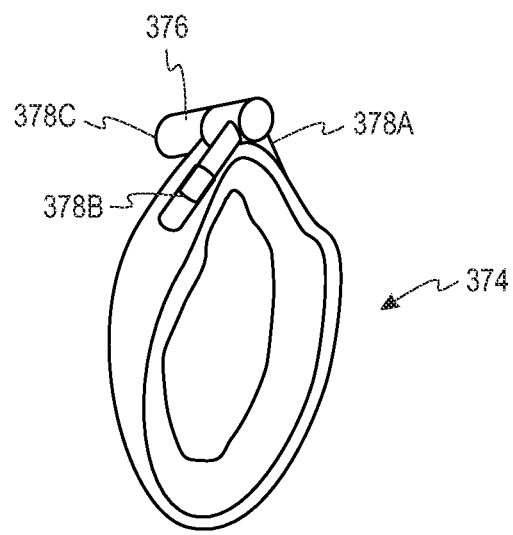
FIG. 3C illustrates a portion of a vacuum tube of the backing member shown in FIG. 3A, according to an example embodiment.
Figure 3D:
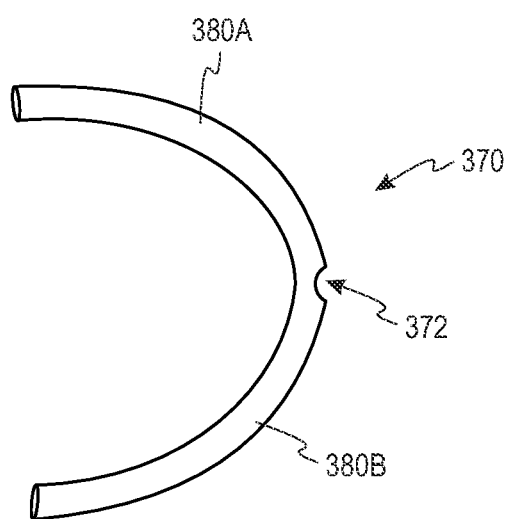
FIG. 3D illustrates a portion of a vacuum tube of the backing member shown in FIG. 3A, according to an example embodiment.

As shown in FIGS. 3A and 3C, the vacuum tube 370 includes a ring-shaped portion 374 extending around the outer portion 320 of the backing member 310. Additionally, the vacuum tube 370 includes a connector 376, which includes a first port 378A, a second port 378B, and a third port 378C. A first section 380A of the ring-shaped portion 374 extends from the first port 378A of the connector 376 to the inlet 372. A second section 380B of the ring-shaped portion 374 extends from the second port 378B of the connector 376 to the inlet 372. A third section 380C extends from the third port 378C of the connector 376 and is suitable to be coupled to a waste collection reservoir such as, for instance, the waste collection reservoir 254 described above.

Further, the vacuum tube 370 can be coupled to a vacuum device such as, for instance, the vacuum device 256 described above. As such, the vacuum device 256 can apply a vacuum pressure, which can cause the vacuum tube 370 to draw urine into the inlet 372 of the vacuum tube 370 at the collection portion 368 of the backing member 310.

In this arrangement, when a user voids and discharges urine from their body, the urine can contact the layer of moisture wicking material 366. The layer of moisture wicking material 366 can then draw the urine toward the collection portion 368 of the backing member 310. At the collection portion 368, the urine can be drawn into the vacuum tube 370 by the vacuum pressure applied by the vacuum device 256. Under the vacuum pressure, the urine can be drawn along the vacuum tube 370 to the waste collection reservoir 254.

In the example of FIGS. 3A-3D, the vacuum tube 370 includes a ring-shaped portion 374, which extends around the outer portion 320 of the backing member 310. By providing the vacuum tube 370 in a ring shape, the vacuum tube 370 can provide structural support to the backing member 310. However, as the vacuum tube 370 can be made of a flexible material, the vacuum tube 370 can be flexed to contour according to a shape of the user's pelvic area adjacent to the backing member 310.

As shown in FIG. 3A, the backing member 310 can also include an adhesive 326 for attaching the backing member 310 to a user. Specifically, in FIG. 3A, the adhesive 326 is provided on an anchor tab 328, which extends over the third section 380C of the vacuum tube 370. This can help to reduce (or prevent) the vacuum tube 370 from accidental pulling and leakage resulting from such pulling.

Figure 4:
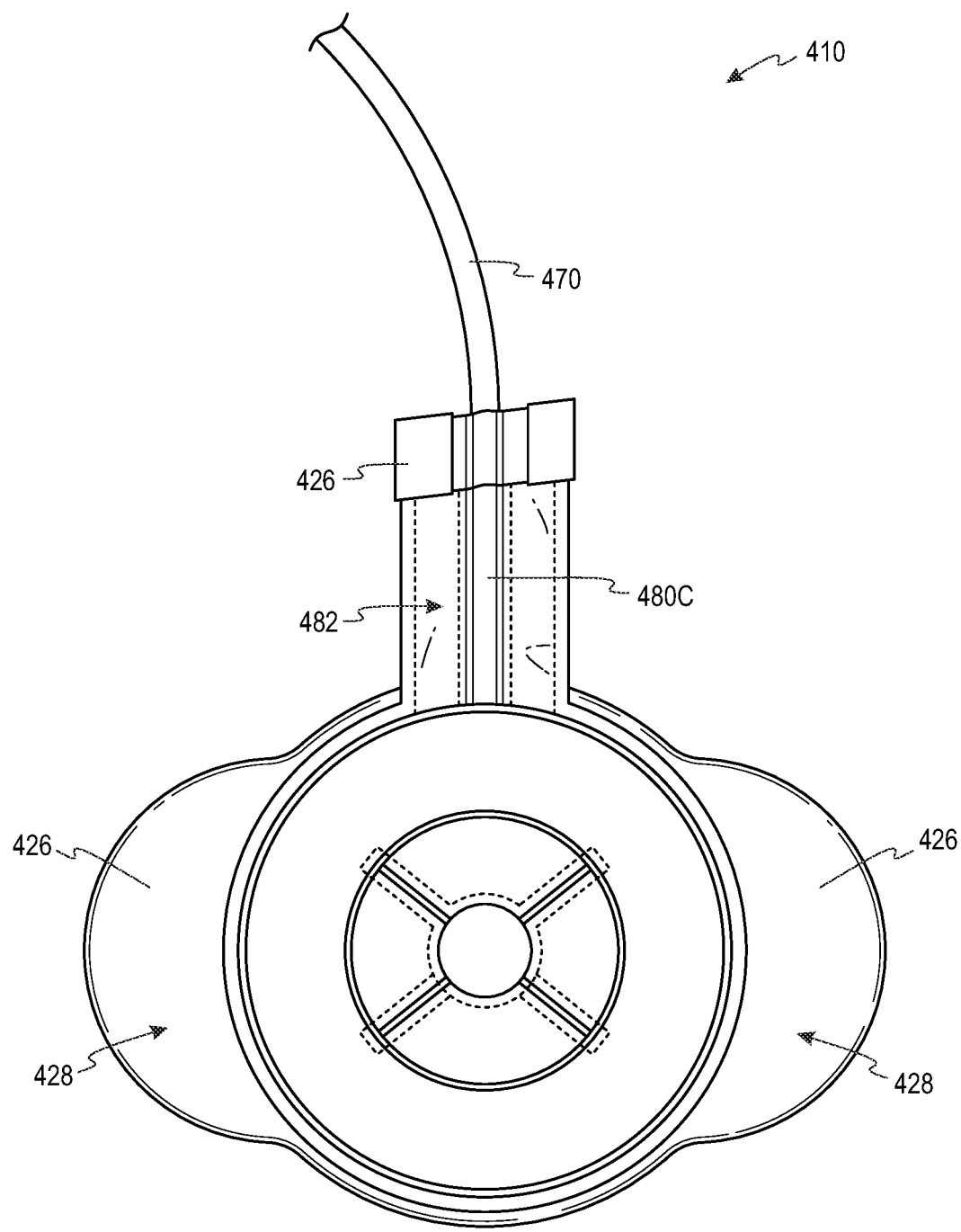
FIG. 4 illustrates a backing member, according to an example embodiment.

In examples shown in FIGS. 1A, 1B, 3A, and 3B, the backing members 110, 310 included a single anchor tab 128, 328 for the adhesive 126, 326. In other examples, the backing members 110, 310 can include more than one anchor tabs 128, 328. For example, FIG. 4 depicts a backing member 410, which includes two anchor tabs 428 having adhesive 426. This arrangement of anchor tabs 428 can facilitate adhering the backing member 410 on opposing sides of the user's pelvic area, which may improve attachment in some instances.

Additionally, the backing member 410 can include an extension portion 482, which extends along a portion of a third section 480C of a vacuum tube 470. The extension portion 482 can also include the adhesive 426. In this arrangement, the extension portion 482 can help to reduce (or prevent) accidental pulling and leakage and/or further improve attachment to the user.

Figure 5:
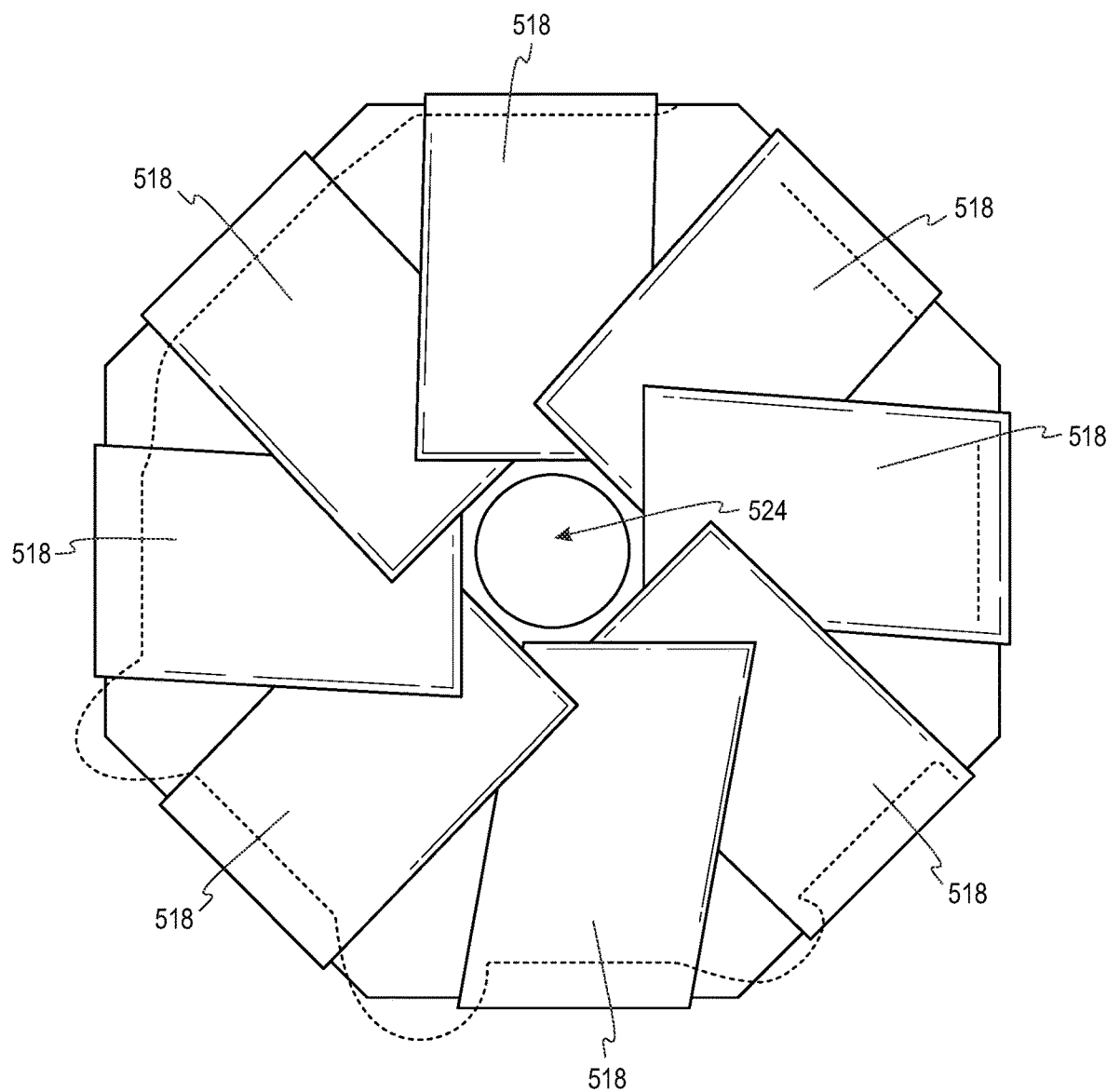
FIG. 5 illustrates a plurality of flexible members of a backing member, according to an example embodiment.

Referring now to FIG. 5, a portion of a backing member is depicted according to another example embodiment. Specifically, FIG. 5 depicts an alternative arrangement for the flexible members 118, 318 described above. For example, as described above, the flexible members 118, 318 are shown in a non-overlapping arrangement relative to each other.

By contrast, FIG. 5 depicts a plurality of flexible members 518, which at least partially overlap each other. As shown in FIG. 5, the flexible members 518 define an aperture 524. Like the flexible members 118, 318 described above, the flexible members 518 are suitable to deflect distally to expand the size of the aperture 524. However, when the flexible members 518 deflect distally, the flexible members 518 can remain in an overlapping arrangement relative to each other. As such, when the flexible members 518 deflect distally, no gaps are formed between adjacent ones of the flexible members 518. This can beneficially assist in preventing leakage of urine from the urine collection device 100.

Figure 6B:
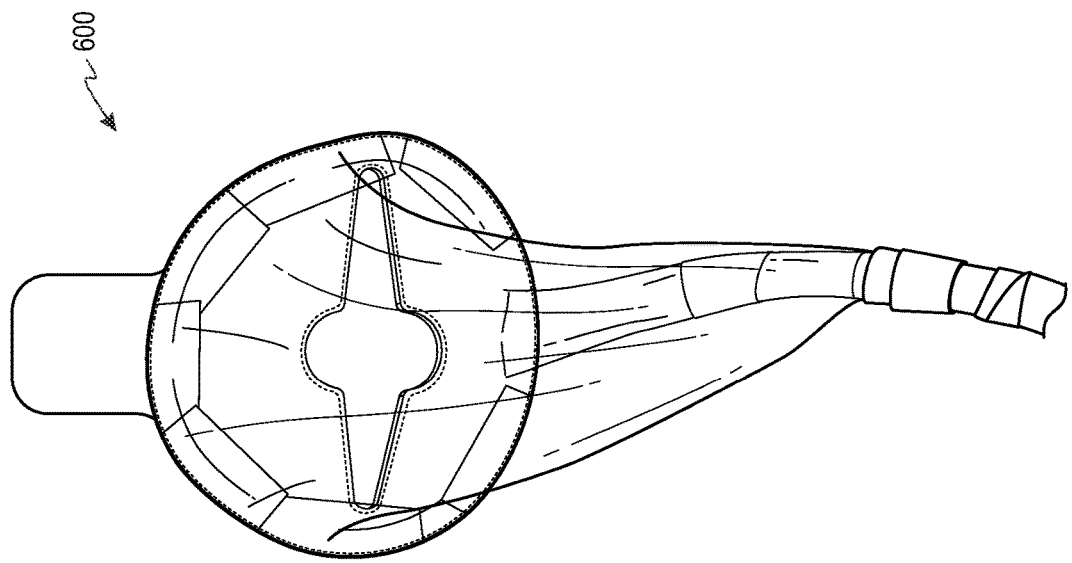
FIG. 6B illustrates another perspective view of the urine collection device shown in FIG. 6A, according to an example embodiment.
Figure 6A:
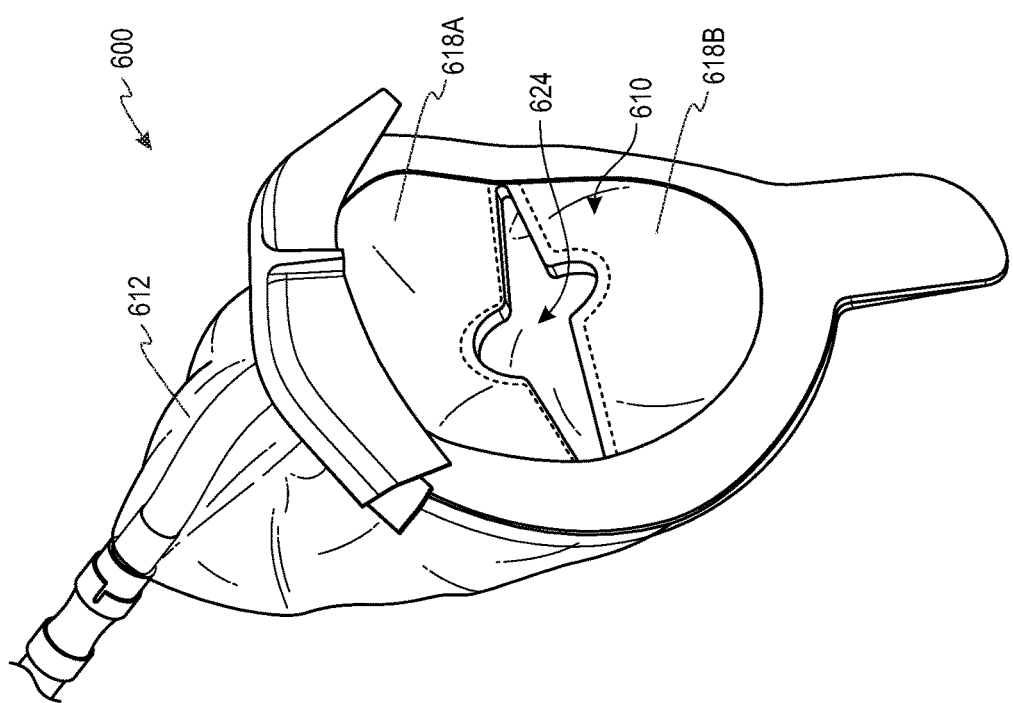
FIG. 6A illustrates a perspective view of a urine collection device, according to an example embodiment.

Referring now to FIGS. 6A-6B, a urine collection device 600 is depicted according to another example embodiment. As shown in FIGS. 6A-6B, the urine collection device 600 includes a backing member 610 coupled to a collection member 612, as described above. The backing member 610 includes a first flexible member 618A and a second flexible member 618B, which define an aperture 624. The first flexible member 618A and the second flexible member 618B are arranged so that the second flexible member 618B can provide a barrier (e.g., a dam), which can beneficially inhibit or prevent urine from leaking out of the collection member 612, when the urine collection device 600 is attached to the user in the orientation depicted in FIGS. 6A-6B. The first flexible member 618A can be made up of a plurality of flex members.

Figure 7C:
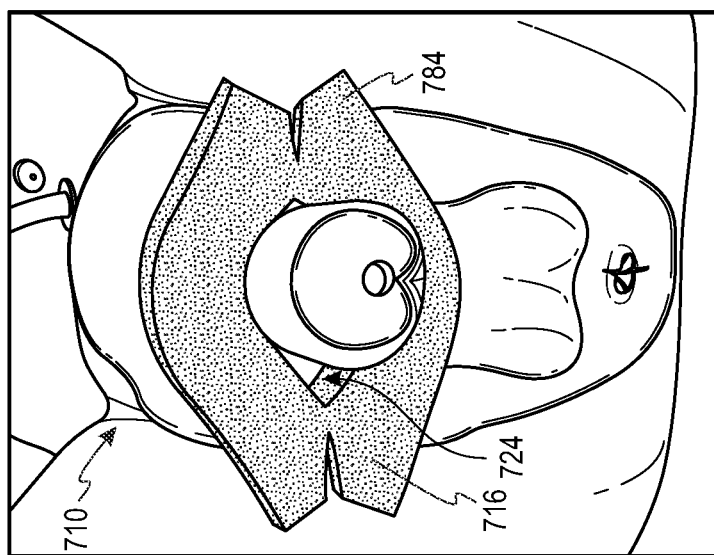
FIG. 7C illustrates the foam member shown in FIG. 7A in a third state, according to an example embodiment.
Figure 7B:
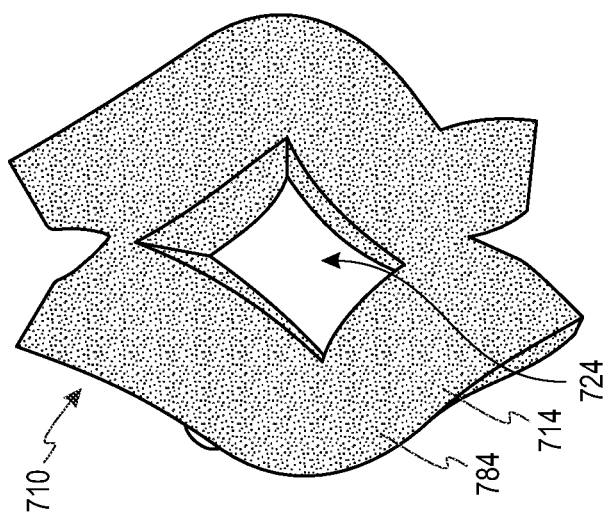
FIG. 7B illustrates the foam member shown in FIG. 7A in a second state, according to an example embodiment.
Figure 7A:
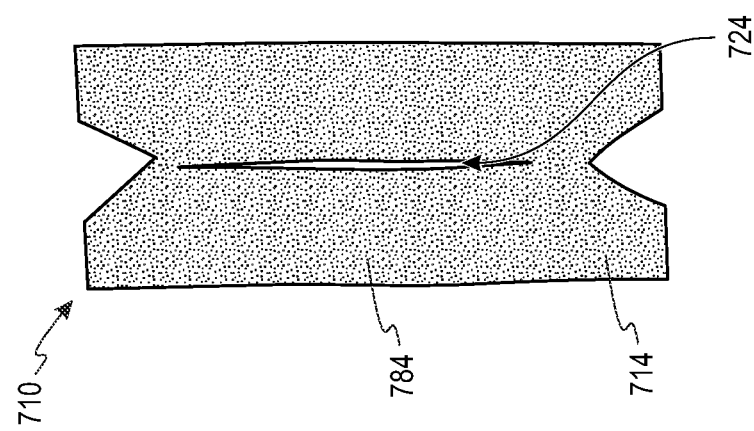
FIG. 7A illustrates a foam member in a first state, according to an example embodiment.

Referring now to FIGS. 7A-7C, a portion of a backing member 710 is depicted according to another example embodiment. In this example, the backing member includes a distal side 716 for facing the collection member 112 and a proximal side 714 opposite the distal side 716. The backing member 710 includes a foam member 784. The foam member includes (i) a liquid impermeable layer on the distal side 716 of the backing member 710, and (ii) a wicking layer for wicking urine on the proximal side 714 of the backing member 710.

Within examples, the foam member 784 can be used in addition or alterative to the flexible members described in the examples above to provide for retention of the backing member 710 on the penis of the user. For example, as shown in FIGS. 7A-7C, the foam member 784 can define an aperture 724. As shown in FIG. 7B, a force can be applied to a top portion and a bottom portion of the foam member 784 (e.g., by a pinching action) to expand the aperture 724. While the aperture is expanded, the penis of the user can be inserted through the aperture 724. After the penis is inserted in the aperture 724, the force can be remove from the top portion and the bottom portion of the foam member 784, which allows the foam member 784 to relax into contact with the penis. In this way, the foam member 784 can provide for retention of the penis within the urine collection device. To remove the foam member 784, a force can be reapplied to the top portion and the bottom portion of the foam member 784 to expand the aperture 724.

As shown in FIG. 7B, the force for expanding the aperture 724 can be conveniently provided using a single hand. This can assist in improving operational efficiency, ease of use, and safety.

Referring now to FIG. 8, a plurality of collection members 812A, 812B, 812C are depicted according to additional examples. The collection members 812A, 812B, 812C can be used in connection with any of the backing members (e.g., the backing members 110, 310, 410, 610, 710) described herein.

The collection members 812A, 812B, 812C are substantially similar to the collection member 112 described above. However, the collection members 812A, 812B, 812C generally have shapes and/or sizes that differ to some extent relative to those of the collection member 112 described above.

Additionally, for example, the collection members 812A, 812B, 812C include at least one of a layer of moisture wicking material 886 or a layer of absorbent material 888 in the internal cavity. The layer of moisture wicking material 886 in the internal cavity can facilitate drawing the urine discharged from a user toward an outlet 830. Similarly, the layer of absorbent material 888 in the internal cavity can facilitate absorbing the urine discharged from the user. As examples, the absorbent material can include a cotton fiber, a cellulose fiber, absorbent polymers, hydrophilic absorbing powder, and/or synthetic fibers.

Figure 9A:
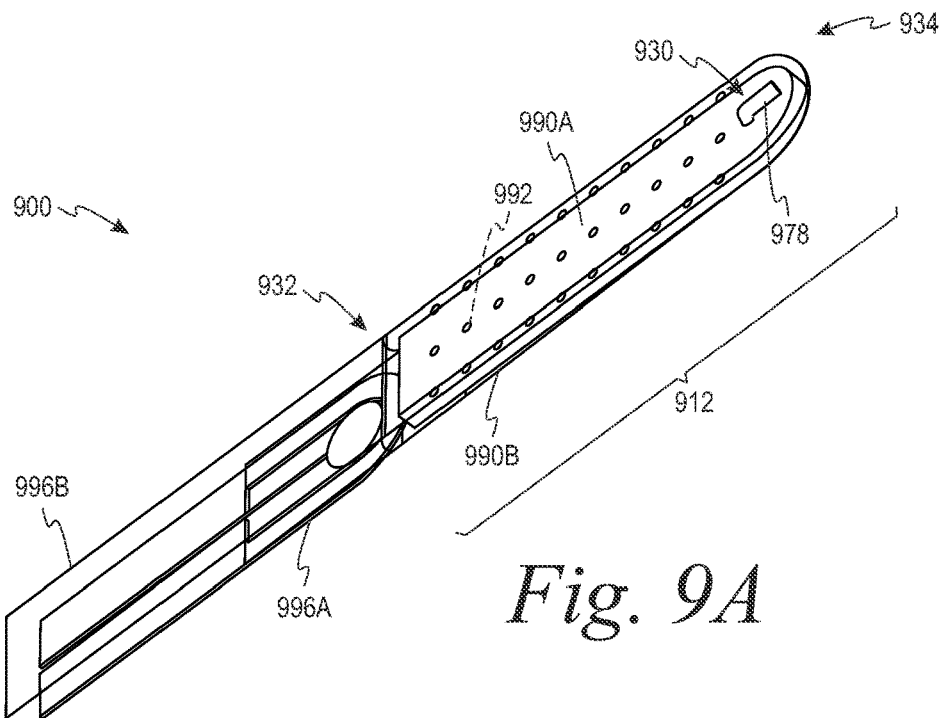
FIG. 9A illustrates a perspective view of a urine collection device, according to another example embodiment.
Figure 9B:
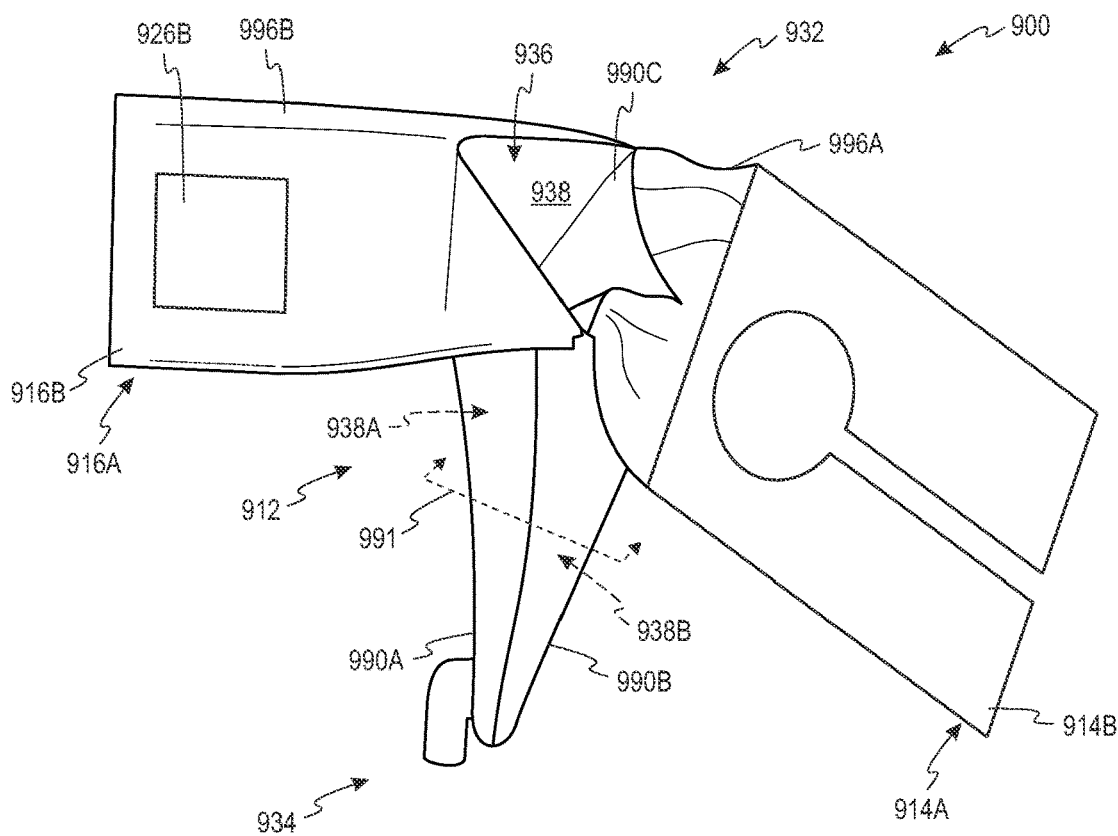
FIG. 9B illustrates another perspective view of the urine collection device shown in FIG. 9A, according to an example embodiment.
Figure 9C:
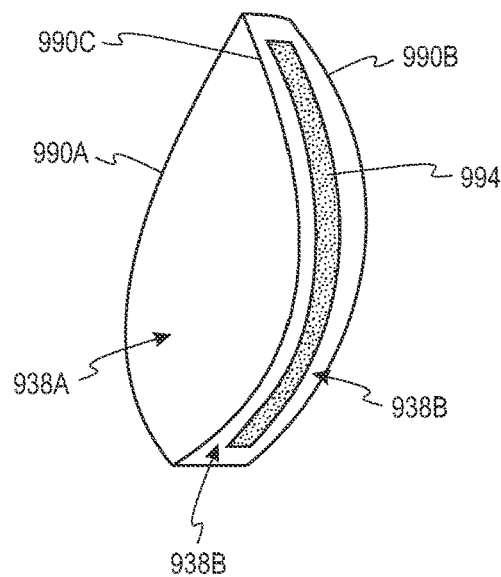
FIG. 9C illustrates a cross-sectional view of the urine collection device shown in FIG. 9B, according to an example embodiment.
Figure 9D:
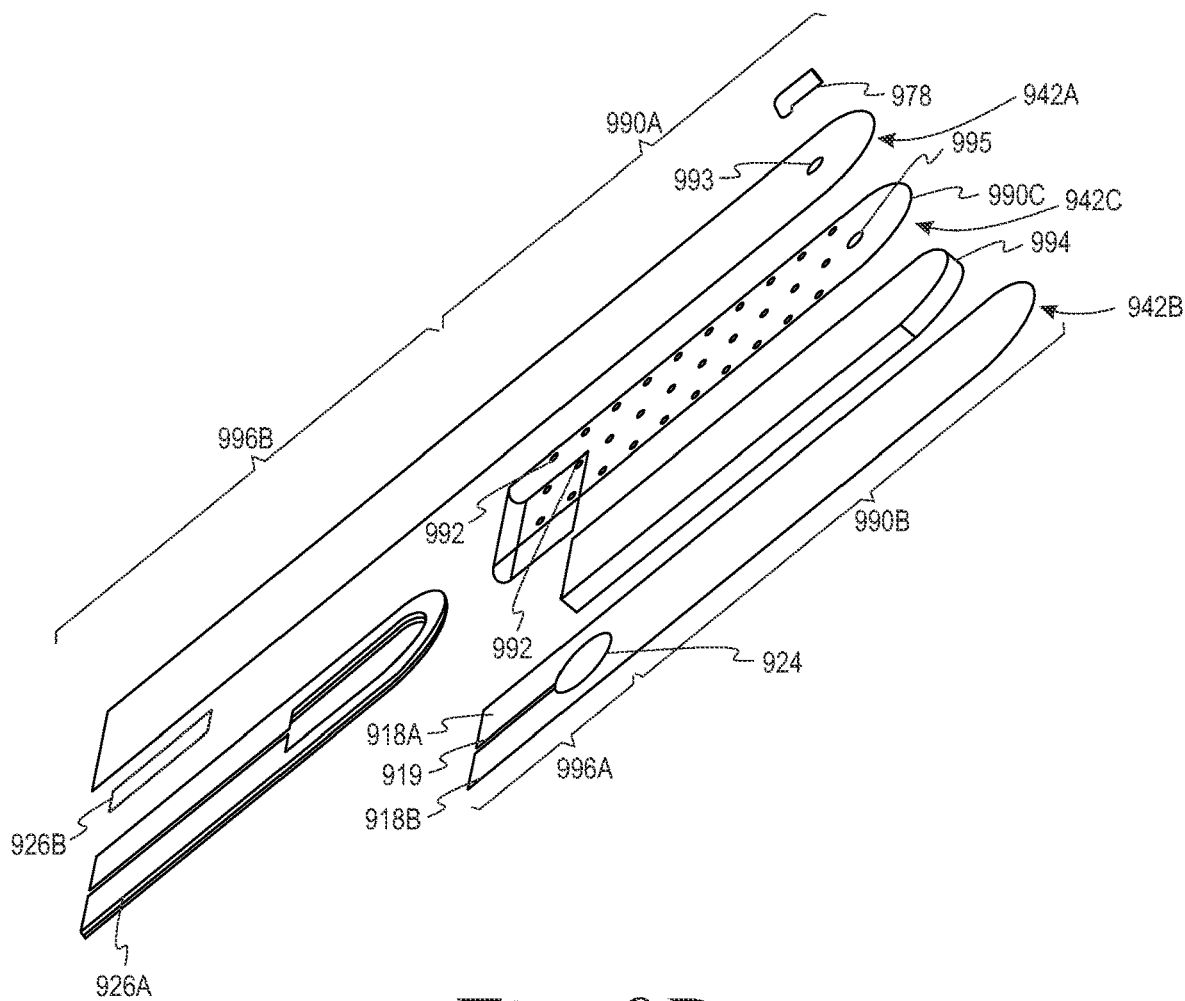
FIG. 9D illustrates an exploded view of the urine collection device shown in FIG. 9A, according to an example embodiment.

Referring now to FIGS. 9A-9D, a urine collection device 900 according to another example embodiment. More specifically, FIG. 9A depicts a perspective view of the urine collection device 900, FIG. 9B depicts another perspective view of the urine collection device 900, FIG. 9C depicts a cross-sectional view of the urine collection device 900 taken through a line 991 in FIG. 9B, and FIG. 9D depicts an exploded view of the urine collection device 900.

As shown in FIGS. 9A-9D, the urine collection device 900 includes a collection member 912 that is suitable to direct urine to an outlet 930 of the collection member 912. The collection member 912 extends from a proximal end 932 to a distal end 934. As shown in FIGS. 9B-9C, the proximal end 932 includes an opening 936 that provides access to an internal cavity 938 of the collection member 912.

As also shown in FIGS. 9A-9D, the collection member 912 includes a top wall 990A, a bottom wall 990B, and inner wall 990C between the top wall 990A and the bottom wall 990B. In this arrangement, the internal cavity 938 includes a first chamber 938A and a second chamber 938B with the inner wall 990C separating the first chamber 938A from the second chamber 938B. As shown in FIGS. 9B-9C, the opening 936 in the collection member 912 is defined by the inner wall 990C and the top wall 990A of the collection member 912. Whereas, at the proximal end 932, the inner wall 990C is coupled to the bottom wall 990B of the collection member 912. As such, the inner wall 990C inhibits access to the second chamber 938B from outside of the first chamber 938A. Thus, when the user inserts a penis through the opening 936, the penis is received in the first chamber 938A of the internal cavity 938.

With the user's penis extending through the opening 936, urine can be initially received in the first chamber 938A of the collection member 912. The received urine can be directed from the first chamber 938A to the second chamber 938B so as to reduce (or minimize) contact between the user and the urine. This can beneficially improve user comfort, and/or improve hygiene and sanitary conditions for the user.

To direct the urine from the first chamber 938A to the second chamber 938B, the first chamber 938A is in communication (i.e., fluid communication) with the second chamber 938B. For example, the inner wall 990C can define a plurality of perforations 992 through which the first chamber 938A can communicate with the second chamber 938B. In FIGS. 9A and 9D, the perforations 992 each have a generally circular shape; however, one or more of the perforations 992 can have a different shape in other example embodiments. Additionally, in FIGS. 9A and 9D, the perforations 992 are arranged in a pattern including three lines of perforations 992 in the inner wall 990C; however, the perforations 992 can be arranged in a different pattern in other example embodiments.

Additionally, to assist in directing the urine in the second chamber 938B to the outlet 930 at the distal end 934, the urine collection device 900 can include a spacer 994 in the second chamber 938B. The spacer 994 can, for example, help to separate the bottom wall 990B from the inner wall 990C. This can help to inhibit (or prevent) an occlusion of the second chamber 938B, which may negatively impact egress of the urine from the urine collection device 900. Additionally, for example, the spacer 994 can help to inhibit (or prevent) an occurrence of a vacuum lock condition due to the vacuum pressure applied by a vacuum device (such as, e.g., the vacuum device 256 depicted in FIG. 2).

In one example, the spacer 994 is an open-cell foam material configured to allow the urine to flow through the spacer 994 in a direction from the proximal end 932 to the distal end 934. In another example, the spacer 994 can be made from other materials such as, for instance, a closed foam material. However, an open-cell foam material can be particularly beneficial in that an open-cell foam material can allow the urine to flow both through and around the spacer 994. Whereas, other materials may limit and/or prevent the urine from flowing through the spacer 994. In some implementations, the open-cell foam material of the spacer 994 can allow the urine in the second chamber 938B to flow to the outlet 930 even when the spacer 994 is compressed.

In one implementation, for instance, the spacer 994 can include a thermally reticulated 45 ppi polyether polyurethane foam (PUR). Additionally, for instance, the spacer 994 can have (i) a pore size (visual) of approximately 40 pores per inch (ppi) to approximately 50 ppi, (ii) a density of approximately 1.3 pounds per cubic foot (lbs/ft$^3$) to approximately 1.6 lbs/ft$^3$, (iii) a tensile strength of at least approximately 10.0 pounds per square inch (psi), (iv) an elongation of 100 percent, (v) a tear of at least approximately 2.5 pounds per inch (lbs/in), (vi) a compression load deflection at 25% R (CLD 25% R(2"×2"×1")) of at least approximately 0.35 psi, (vii) a CLD 65% R(2"×2"×1") of at least approximately 0.43 psi, and/or (viii) a maximum compression set of approximately 15%.

In another example, for instance, the spacer 994 can include a plurality of gas filled pockets separated by gaps, which allow the urine to flow through and around the spacer 994. For example, the pockets can be similar to bubble wrap (e.g., made from (e.g., polyethylene pockets filled with air). A quantity, a size, and/or a density of the pockets can be arranged to allow for urine flow to the outlet 930 while inhibiting a vacuum lock condition when a vacuum pressure is applied to the urine collection device 900. In a further example, the spacer 994 can be constructed with a plurality of channels to allow the urine to flow to the outlet 930 while also allowing for air to flow, alleviating a vacuum lock condition. In one implementation, the spacer 994 can be made from a polymer material and molded, for example, by an injection molding or thermoformed molding process. Other examples are also possible.

As noted above, the collection member 912 can be made from a flexible material such as, for instance, silicone, rubber, latex, and/or a thermoplastic. The spacer 994 can also beneficially assist in providing support to the urine collection device 900 to, for instance, inhibit (or prevent) twisting of the collection member 912 and/or improve handling of the urine collection device 900. In FIGS. 9A and 9D, the spacer 994 extends from the proximal end 932 to the distal end 934. This can allow the spacer 994 to help to support the collection member 912 over a relatively large portion of the urine collection device 900. However, in other examples, the spacer 994 can extend over a smaller portion of the second chamber 938B.

As noted above, the collection member 912 is suitable to (i) direct urine from the first chamber 938A to the second chamber 938B (e.g., via the perforations 992) and (ii) direct the urine in the second chamber 938B distally toward the outlet 930 (e.g., through and/or around the spacer 994). The outlet 930 is configured to egress the urine from internal cavity 938 of the collection member 912. For example, the outlet 930 can include an aperture 993 in the top wall 990A and a port 978, which is suitable to be coupled to a drain tube (e.g., a drain tube 252 shown in FIG. 2). The port 978 can be coupled to the top wall 990A at the aperture 993 by, for example, RF heat sealing and/or RF welding.

In one example, the port 978 can include a thread for threadably coupling with the drain tube. In another example, the port 978 can include a hose barb and/or a Luer lock for coupling with the drain tube. In another example, as described in further detail below, the port 978 can include a tapered end portion for coupling with the drain tube. Given that drain tubes may have different sizes (e.g., depending on the make and/or model of the vacuum device 256), the tapered end portion of the port 978 can help to more universally couple the port 978 to a plurality of differently sized drain tubes.

In FIGS. 9A-9D, the outlet 930 is at a location spaced away from the distal end 934. As described in further detail below, the outlet 930 can be at other locations such as, for example, at a distalmost point of the collection member 912 in other examples. By locating the outlet 930 near or at the distal end 934, pooling of urine at the distal end 934 can be reduced (or minimized).

As noted above, the collection member 912 is suitable to (i) direct urine from the first chamber 938A to the second chamber 938B and (ii) direct the urine in the second chamber 938B distally toward the outlet 930. To facilitate egressing the urine in the second chamber 938B from the collection member 912, the inner wall 990C can include a passage 995 at the outlet 930. The passage 995 can be similar to the perforations 992 in the inner wall 990C in that the passage 995 provides for communication between the second chamber 938B and the first chamber 938A. In one example, the passage 995 can have a size that is greater than a size of each of the perforations 992. Additionally, the passage 995 can be aligned with outlet 930 of the collection member 912 (e.g., aligned with the aperture 993 in the top wall 990A). In this arrangement, when the vacuum device applies the vacuum pressure to the outlet 930, the urine can be directed under suction (i) from the second chamber 238B to the first chamber 238A via the passage 995 (and/or adjacent ones of the perforations 992), and (ii) from the first chamber 238A into the drain tube via the outlet 930.

Although the passage 995 is larger than each perforation 992 in FIGS. 9A-9D, the passage 995 can have a size that is the same as and/or smaller than one or more of the perforations 992 in other examples. However, providing the passage 995 with a size that is larger than the perforations 992 can help to receive and/or maintain the urine in the second chamber 938B in areas proximal to the outlet 930 (e.g., as the urine is flowing in a direction from the proximal end 932 toward the distal end 934).

Additionally, as noted above, the passage 995 is aligned with the outlet 930 in FIGS. 9A-9D. This can, for example, help to apply the vacuum pressure more directly to the urine in the second chamber 938B when the outlet 930 is on the top wall 990A. However, the passage 995 can be at other locations relative to the outlet 930 in other examples. Further, although the passage 995 is distal of the perforations 992 in FIGS. 9A-9D, one or more of the perforations can be distal of the passage 995 in other examples.

As described above, when the user inserts a penis through the opening 936, the penis is received in the first chamber 938A of the internal cavity 938. Within examples, the first chamber 938A of the collection member 912 can have a size and shape that provides for the collection member 912 loosely enveloping the penis when inserted through the opening 936. For instance, in one implementation, at least a portion of the collection member 912 at the first chamber 938A can have a circumference, which is greater than most (or all) penis sizes. By loosely enveloping the penis, the collection member 912 can reduce (or minimize) discomfort of the user relative to condom catheters, for example.

As shown in FIGS. 9A-9D, the urine collection device 900 further includes one or more attachment members 996A-996B that are suitable to secure the urine collection device 900 to a user. In particular, in FIGS. 9A-9D, the urine collection device 900 includes a first attachment member 996A and a second attachment member 996B. However, the urine collection device 900 can include a single attachment member 996A-996B or more than two attachment members 996A-996B in other examples.

The first attachment member 996A extends from the bottom wall 990B of the collection member 912 at the proximal end 932. The first attachment member 996A includes an outer side 914A for contacting a pelvic area of a user and an inner side 914B facing the collection member 912 when the urine collection device 900 is secured to the user. The first attachment member 996A also defines an aperture 924, which extends through the first attachment member 996A from the outer side 914A to the inner side 914B. When the urine collection device 900 is secured to the user, the first attachment member 996A receives the penis of the user in the aperture 924 with the outer side facing the pelvic area of the user and the inner side facing the collection member 912.

As shown in FIGS. 9A-9B and 9D, the first attachment member 996A also includes a plurality of flexible members 918A-918B that facilitate access to the aperture 924. Specifically, in FIGS. 9A-9D, the first attachment member 996A includes a first flexible member 918A and a second flexible member 918B that are movable relative to each other to facilitate access to the aperture 924 in the first attachment member 996A. For example, as shown in FIG. 9D, the first flexible member 918A can be separated from the second flexible member 918B by a slit 919 extending distally from the aperture 924 in the first attachment member 996A. In FIG. 9D, the slit 919 extends from the aperture 924 to a distalmost point of the first attachment member 996A. However, the slit 919 can extend to a point that is proximal of the distalmost point of the first attachment member 996A in another example embodiment.

In this arrangement, to receive the penis through the aperture 924, the first flexible member and the second flexible member can be deflected away from each other to expand the size of the aperture 924. After the aperture 924 is expanded, the first attachment member 996A can be positioned on the user with the penis extending through the aperture 924. After the first attachment member 996A is positioned on the user such that the penis extends through the aperture 924, the first flexible member 918A and the second flexible member 918B can be moved back toward each other to reduce the size of the aperture 924 to a size that comfortably fits around the penis. As such, the first flexible member 918A and the second flexible member 918B can be manipulated to adjust the size of the aperture 924 and thereby accommodate a specific size and/or shape of a given user's penis.

In some examples, when the penis is inserted through the aperture 924, the first flexible member 918A and the second flexible member 918B can additionally apply a force on the penis that assists in retaining the penis in a desired position relative to the collection member 912. As the size of the aperture 924 can expand to an extent commensurate with the size of the particular user's penis, the first attachment member 996A can provide a more universal fit for a relatively broad range of the male population.

The first attachment member 996A can include a first adhesive 926A to further assist in securing the first attachment member 996A to a user. For instance, the first adhesive 926A can be coupled to the outer side 914A of the first attachment member 996A. As such, when the first attachment member 996A is secured to the user, the first adhesive 926A on the outer side 914A of the first attachment member 996A can contact and adhere to the pelvic area of the user to assist in retaining the urine collection device 900 in the desired position. By providing the first adhesive 926A on the outer side 914A, which contacts the pelvic area of the user, the first adhesive 926A can more comfortably adhere the urine collection device 900 to a less sensitive part of the body than a condom catheter.

As shown in FIGS. 9A and 9D, the first adhesive 926A can have a shape that generally corresponds to a shape of the first attachment member 996A. For instance, the first adhesive 926A can extend around at least a portion of the aperture 924, along at least a portion of the first flexible member 918A, and along at least a portion of the second flexible member 918B. This can help to secure the first attachment member 996A to the user over a relatively large surface area of the first attachment member 996A, which can help to maintain the urine collection device 900 in a desired position relative to the user. Also, in some examples, the first adhesive 926A can extend entirely around the aperture 924 in the first attachment member 996A.

As shown in FIGS. 9A, 9B, and 9D, the second attachment member 996B extends from the top wall 990A of the collection member 912 at the proximal end 932. The second attachment member 996B includes an inner side 916B for contacting a pelvic area of a user and an outer side 916A facing away from the user when the urine collection device 900 is secured to the user. Additionally, the second attachment member 996B includes a second adhesive 926B to assist in securing the second attachment member 996B to the user. Specifically, the second adhesive 926B is coupled to the inner side 916B of the second attachment member 996B.

In some examples, the second attachment member 996B can have a length (i.e., a dimension along a longitudinal axis) that is greater than a length of the first attachment member 996A. This can assist in allowing the second attachment member 996B to be secured to the user at a location that is above a location at which the first attachment member 996A is secured to the user.

As shown in FIG. 9D, the urine collection device 900 can include a plurality of sheets 942A-942C of material. In particular, the urine collection device 900 can include a first sheet 942A, a second sheet 942B, and a third sheet 942C, which are coupled to each other to form the urine collection device 900. As examples, the sheets 942A-942C can be coupled to each other by, for instance, radio frequency (RF) heat sealing and/or RF welding.

The first sheet 942A can provide the top wall 990A of the collection member 912 and the first attachment member 996A, and the second sheet 942B can provide the bottom wall 990B and the second attachment member 996B of the collection member 912. The third sheet 942C is between the first sheet 942A and the second sheet 942B.

In this arrangement, the third sheet 942C can provide the inner wall 990C that divides the internal cavity 938 into the first chamber 938A and the second chamber 938B. Specifically, the first chamber 938A can be defined by a space between the first sheet 942A and the second sheet 942B (i.e., between the top wall 990A and the inner wall 990C), whereas the second chamber 938B can be defined by a space between the second sheet 942B and the third sheet 942C (i.e., between the inner wall 990C and the bottom wall 990B).

In FIG. 9D, the first attachment member 996A is integrally formed with the top wall 990A and the second attachment member 996B is integrally formed with the bottom wall 990B. This can beneficially reduce (or minimize) a risk of the first attachment member 996A and/or the second attachment member 996B becoming detached from the collection member 912. However, in other examples, the first attachment member 996A can be coupled to the top wall 990A and/or the second attachment member 996B can be coupled to the bottom wall 990B.

Figure 10A:
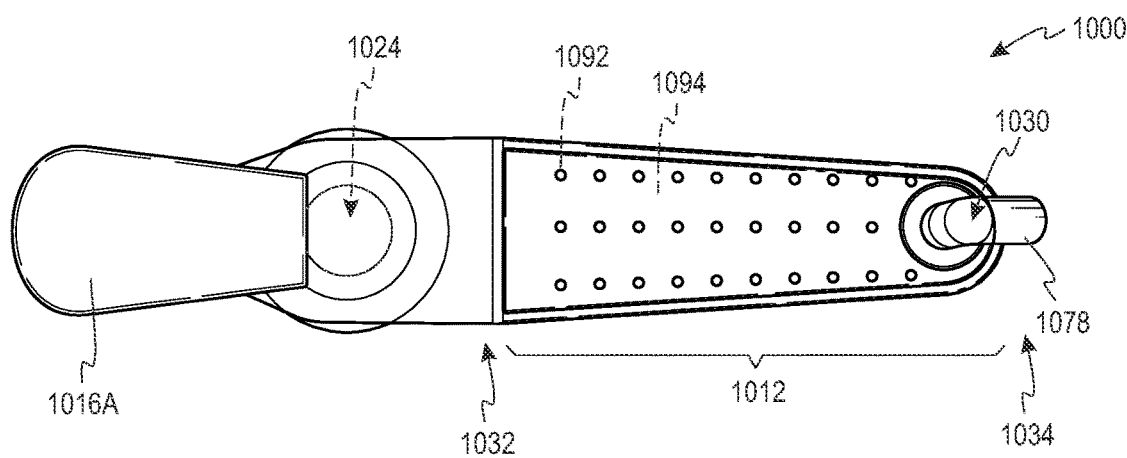
FIG. 10A illustrates a top view of a urine collection device, according to another example embodiment.
Figure 10B:
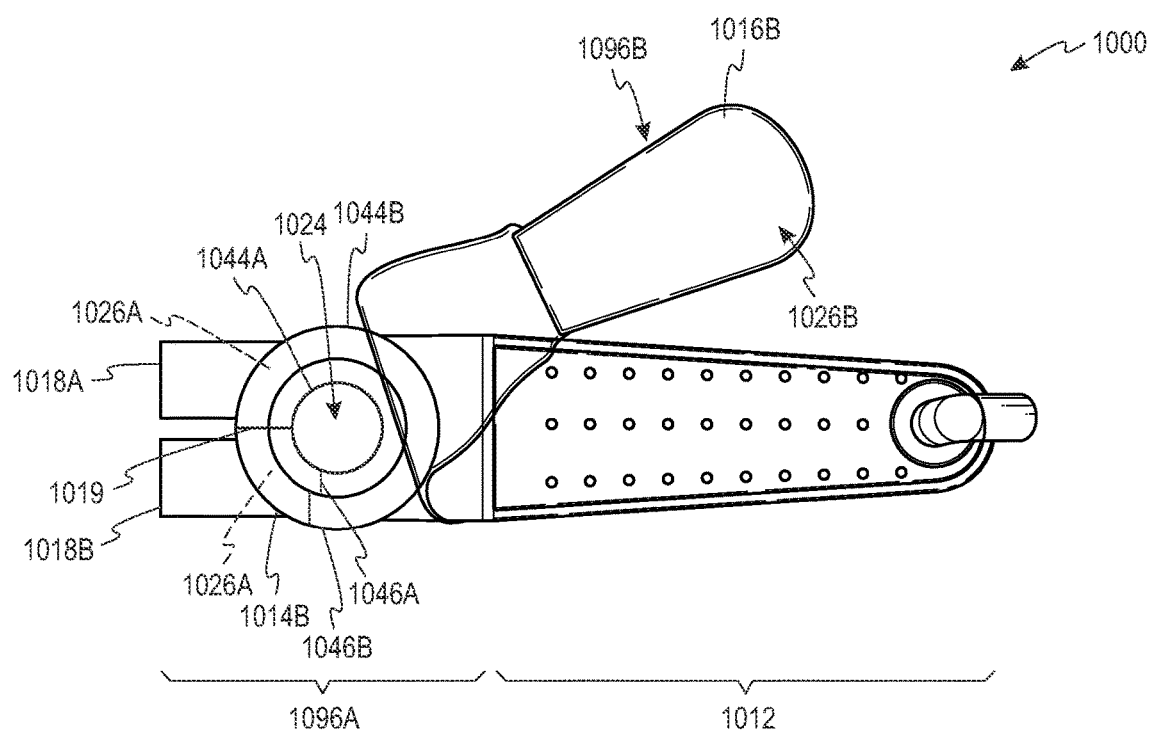
FIG. 10B illustrates another top view of the urine collection device shown in FIG. 10A, according to an example embodiment.
Figure 10C:
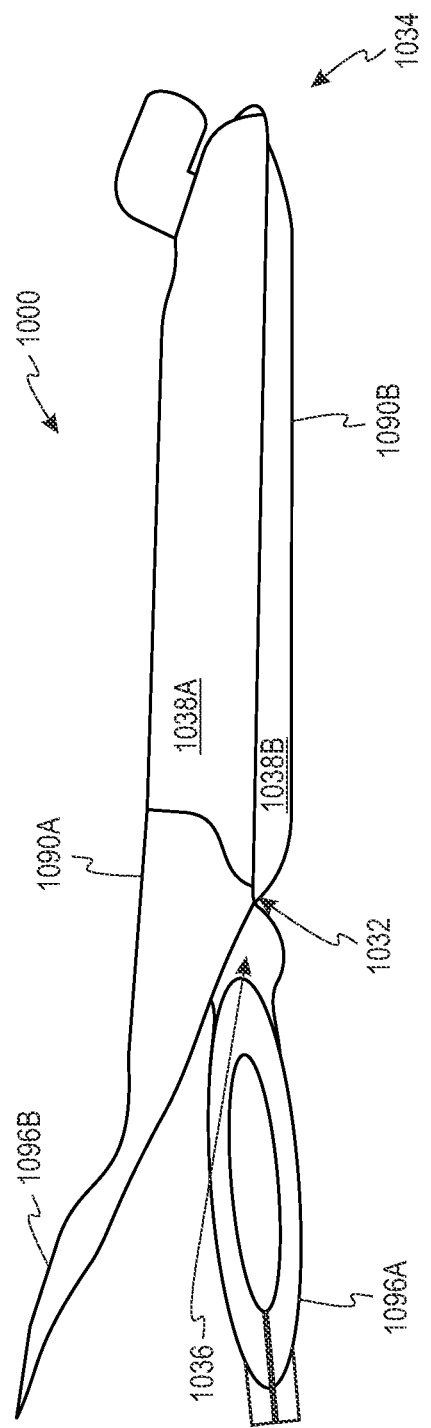
FIG. 10C illustrates a side view of the urine collection device shown in FIG. 10A, according to an example embodiment.

Referring now to FIGS. 10A-10C, a urine collection device 1000 is depicted according to another example embodiment. The urine collection device 1000 is substantially similar to the urine collection device 900 illustrated and described with respect to FIGS. 9A-9D, except the urine collection device 1000 includes attachment members that differ in some ways from the first attachment member 996A and the second attachment member 996B in FIGS. 9A-9D.

As shown in FIGS. 10A-10C, the urine collection device 1000 includes a collection member 1012 extending from a proximal end 1032 to a distal end 1034. As shown in FIGS. 10A-10B, the collection member 1012 has a width that tapers inwardly along a longitudinal axis from the proximal end 1032 to the distal end 1034. As shown in FIG. 10C, the proximal end 1032 includes an opening 1036 that provides access to an internal cavity 1038, which has a first chamber 1038A in communication (i.e., fluid communication) with a second chamber 1038B. The urine collection device 1000 includes an inner wall 1090C separating the first chamber 1038A from the second chamber 1038B and the inner wall 1090C includes a plurality of perforations 1092 through which the first chamber 1038A communicates with the second chamber 1038B. A spacer 1094 is in the second chamber 1038B. Additionally, the urine collection device 1000 includes an outlet 1030 for egressing urine from the internal cavity 1038 of the collection member 1012.

In FIGS. 10A-10C, a first attachment member 1096A extends from a bottom wall 1090B of the collection member 1012 at the proximal end 1032, and a second attachment member 1096B extends from a top wall 1090A of the collection member 1012 at the proximal end 1032. The first attachment member 1096A includes an inner side 1014B and an outer side opposite the inner side 1014B in FIG. 10B, and the second attachment member 1096B includes an outer side 1016A and an inner side 1016B. The first attachment member 1096A also includes a first adhesive 1026A on the outer side of the first attachment member 1096A (i.e., on the side opposite the inner side 1014B shown in FIG. 10B), and the second attachment member 1096B includes a second adhesive 1026B on the inner side 1016B of the second attachment member 1096B to assist in securing the urine collection device 1000 to a user.

As shown in FIG. 10B, the first attachment member 1096A includes a first flexible member 1018A and a second flexible member 1018B. The first flexible member 1018A and the second flexible member 1018B of the first attachment member 1096A define an aperture 1024 in the first attachment member 1096A. As shown in FIG. 10B, the first flexible member 1018A and the second flexible member 1018B are separated by a slit 1019 and are independently movable relative to each other (and/or the collection member 1012).

As shown in FIG. 10B, the first attachment member 1096A includes a ring-shaped portion extending between an inner edge 1044A and an outer edge 1044B. The inner edge 1044A defines a circumference of the aperture 1024 in the first attachment member 1096A, and outer edge 1044B defines a circumference of the ring-shaped portion of the first attachment member 1096A. In this arrangement, the first flexible member 1018A and the second flexible member 1018B can each define a respective semi-circular arc.

In one example, the inner edge 1044A can be a circle having a diameter of approximately 20 millimeters (mm) and the outer edge 1044B can have a diameter of approximately 40 mm. This can allow for a size of the aperture 1024 of the first attachment member 1096A to be dynamically adjusted within a range of sizes between approximately 20 mm and 40 mm based on, among other things, a position of the first flexible member 1018A and the second flexible member 1018B relative to each other. As explained below, the aperture 1024 can be dynamically expanded to accommodate penises having different sizes and/or shapes and thereby provide a more universal fit than existing urine collection devices (e.g., condom catheters). For instance, to accommodate penises having sizes between 20 mm and 40 mm, conventional condom catheters are typically required to come in five or more different sizes (e.g., a 21 mm size catheter, a 25 mm size catheter, a 28 mm size catheter, a 30 mm size catheter, a 35 mm size catheter, and a 40 mm size catheter).

As also shown in FIG. 10B, the ring-shaped portion of the first attachment member 1096A further includes an inner portion 1046A and an outer portion 1046B. The first adhesive 1026A is coupled to the outer portion 1046B, and the inner portion 1046A extends from the outer portion 1046B to the inner edge 1044A. Within examples, the first adhesive 1026A can include a stiffening member that enhances the rigidity of a portion of the first attachment member 1096A coupled to the first adhesive 1026A. For instance, the first adhesive 1026A can include a flexible cushion, which can enhance the rigidity of the outer portion 1046B of the first attachment member 1096A and/or improve user comfort.

In this arrangement, the first attachment member 1096A is configured such that the inner portion 1046A can deflect relative to the outer portion 1046B. This can beneficially provide for the inner portion 1046A deflecting distally relative to the outer portion 1046B when the user's penis is inserted and/or received through the aperture 1024, and thereby expanding the size of the aperture 1024 to accommodate differently sized and shaped penises. The relatively flexible inner portion 1046A can additionally or alternatively improve patient comfort by reducing (or minimizing) an amount of pressure applied by the first attachment member 1096A to the penis.

In the example shown in FIGS. 9A-9D, the first adhesive 926A extends proximally from the first attachment member 996A. By contrast, in FIGS. 10A-10C, the first adhesive 1026A is generally co-extensive with the first attachment member 1096A.

Figure 11A:
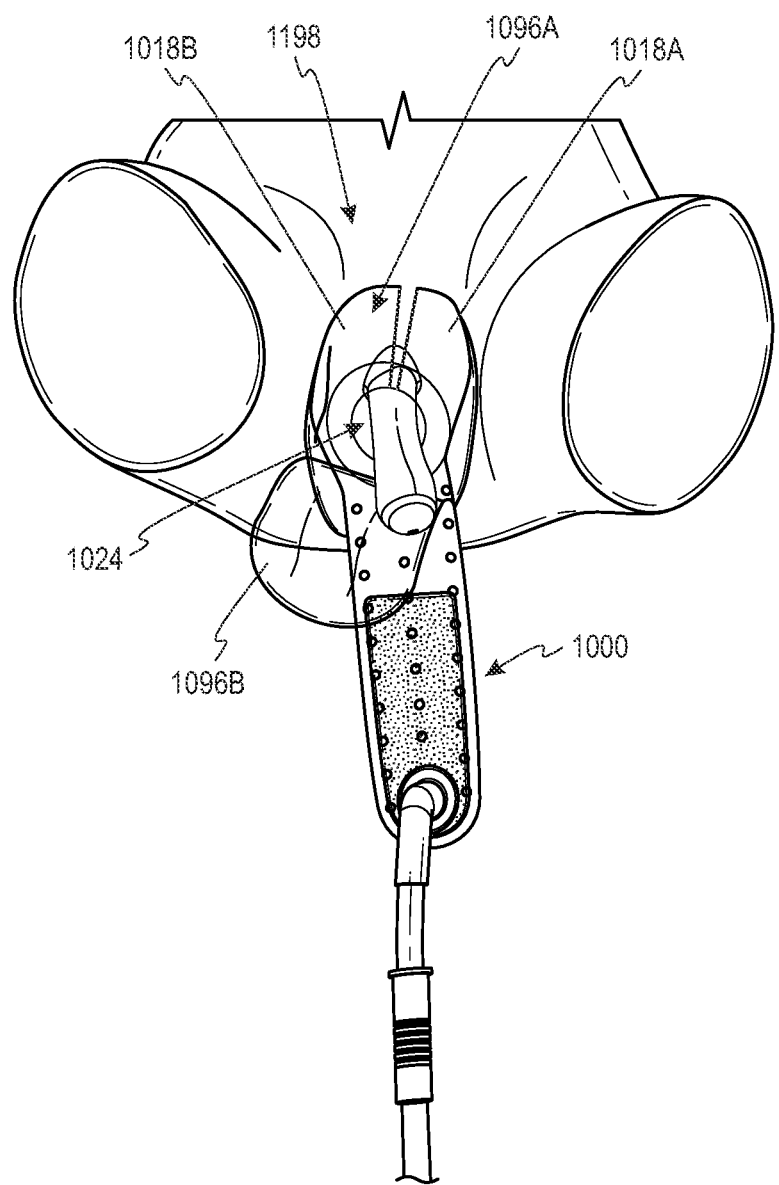
FIG. 11A illustrates a first stage of a process for using the urine collection device shown in FIGS. 10A-10C, according to an example embodiment.
Figure 11B:
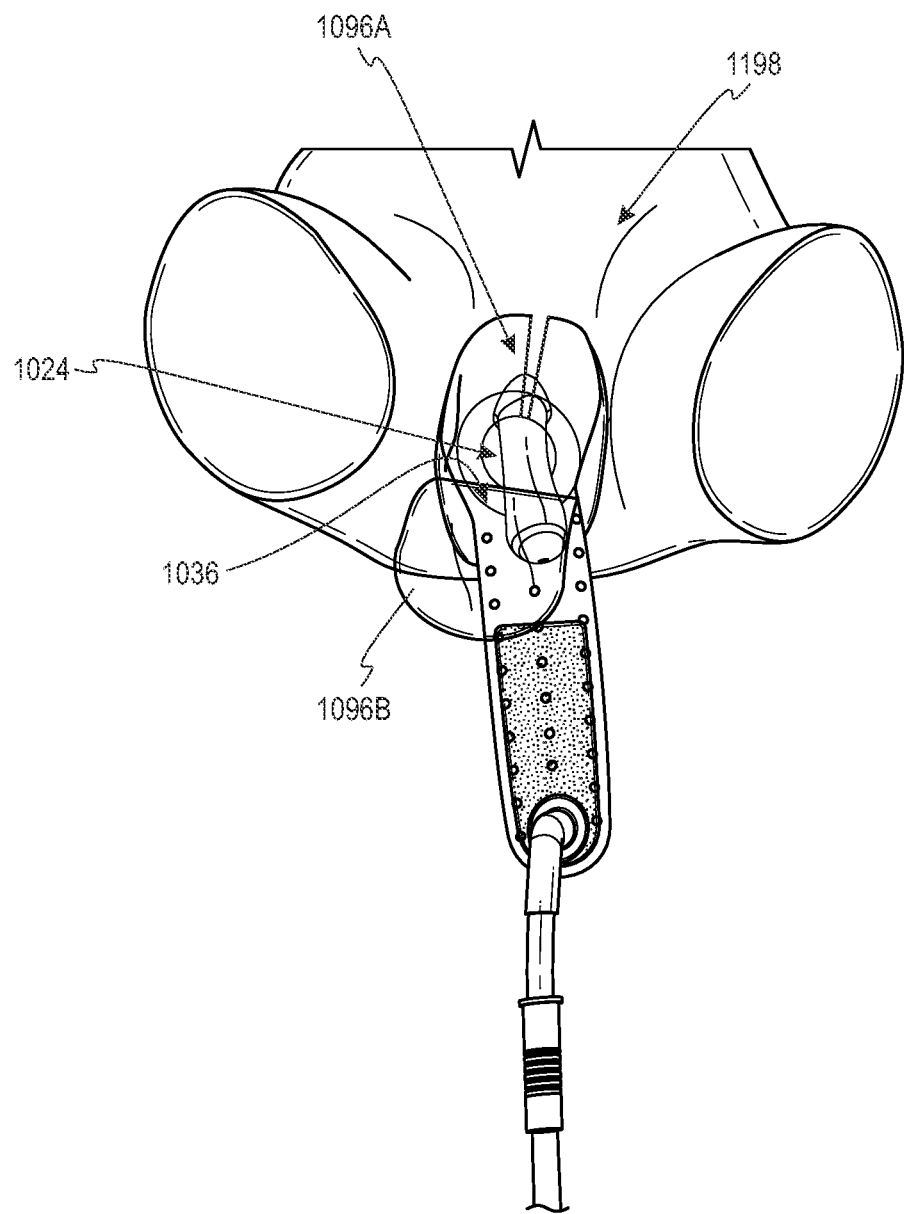
FIG. 11B illustrates a second stage of a process for using the urine collection device shown in FIGS. 10A-10C, according to an example embodiment.
Figure 11C:
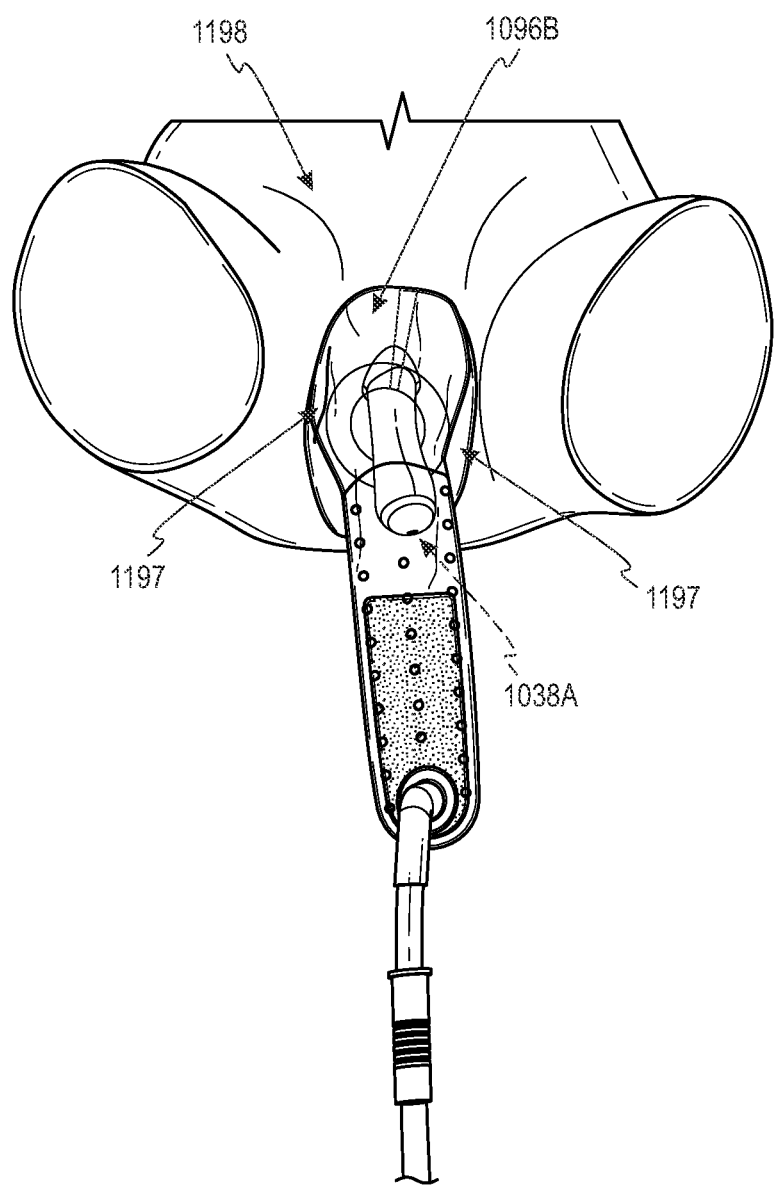
FIG. 11C illustrates a third stage of a process for using the urine collection device shown in FIGS. 10A-10C, according to an example embodiment.

Referring now to FIGS. 11A-11C, a process for using the urine collection device 1000 is depicted according to an example embodiment. To secure the urine collection device 1000 to a user, the first flexible member 1018A and the second flexible member 1018B are moved away from each other to expand the size of the aperture 1024 in the first attachment member 1096A. Next, the first attachment member 1096A is positioned on a pelvic area 1198 of the user such that the penis of the user extends through the aperture 1024. For instance, in one implementation, the first attachment member 1096A can be first moved to a position directly below the penis and then, while the aperture 1024 is expanded, raised until the penis is received in the aperture 1024. That is, the penis can pass through the slit 1019 between the first flexible member 1018A and the second flexible member 1018B to position the penis in the aperture 1024. In another implementation, the first attachment member 1096A can be positioned such that the aperture 1024 is aligned with the penis and then the first attachment member 1096A can be moved proximally to insert the penis through the aperture 1024.

After the penis is received in the aperture 1024, the first flexible member 1018A and the second flexible member 1018B can be moved toward each other to reduce the size of the aperture 124, and the first attachment member 1096A can be coupled to the pelvic area 11098 of the user by the first adhesive 1026A. In this way, the first attachment member 1096A can provide for dynamically adjusting the size of the aperture 1024 to accommodate the specific size and/or shape of the penis, as described above.

FIG. 11A depicts the first attachment member 1096A secured to the pelvic area 1198 of the user with the penis of the user extending through the aperture 1024 in the first attachment member 1096A. Additionally, in FIG. 11A, the penis is outside of the first chamber 1038A of the collection member 1012. Next, the second attachment member 1096B can be moved so that the penis is inserted through the opening 1036. FIG. 11B depicts the urine collection device 1000 with the user's penis extending through the aperture 1024 of the first attachment member 1096A and the opening 1036 of the collection member 1012 into the first chamber 1038A of the collection member 1012. As shown in FIG. 11C, after the penis is inserted into the first chamber 1038A, the second attachment member 1096B is secured to the pelvic area 1198 of the user by the second adhesive 1026B.

Additionally, as shown in FIG. 11C, when the urine collection device 1000 secured to the user, a gap 1197 is formed between the first attachment member 1096A and the second attachment member 1096B on opposing sides of the urine collection device 1000. The gaps 1197 can beneficially allow for air flow through the opening 1036 and into the first chamber 1038A. This air flow can beneficially help to, for example, maintain sanitary conditions and/or improve user comfort. Additionally, for example, the airflow provided by the gaps can help to reduce (or minimize) a risk of a vacuum lock condition occurring.

With the urine collection device 1000 secured to the user as shown in FIG. 11C, the user's penis is received in the first chamber 1038A and above the second chamber 1038B. When the user urinates, the urine is initially received in the first chamber 1038A. The urine is then directed from the first chamber 1038A to the second chamber 1038B via the perforations 1092 in the inner wall 1090C. As the first chamber 1038A is separated from the second chamber 1038B by the inner wall 1090C, contact between the user's penis and the urine is reduced or minimized. Additionally, the spacer 1094 in the second chamber 1038B can assist in maintaining the penis at an elevated position relative to the urine in the second chamber 1038B and, thus, can help to further reduce or minimize contact between the user's penis and the urine. By reducing or minimizing contact between the user's penis and the urine, the urine collection device 1000 improves sanitary conditions, reduces the risk of infection, and/or improves user comfort.

The urine in the second chamber 1038B can be directed distally toward the outlet 1030. At the outlet 1030, the urine can be egressed from the collection member 1012, for example, under a vacuum pressure applied by a vacuum device (e.g., the vacuum device 256) and a drain tube 1052 coupled to the outlet 1030 of the collection member 1012.

Figure 12:
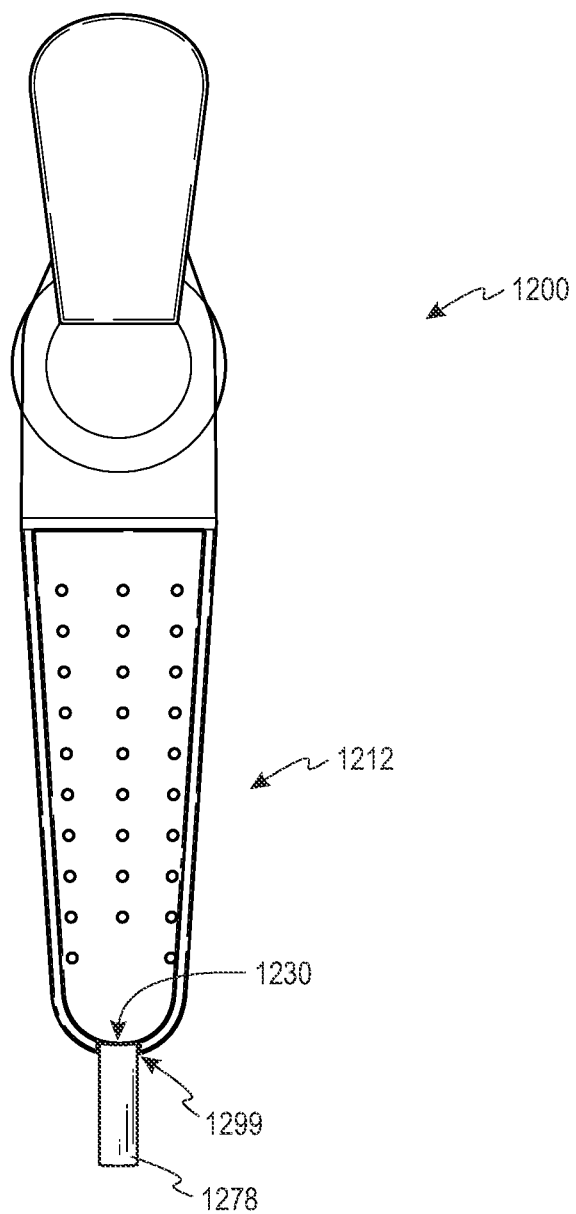
FIG. 12 illustrates a top view of a urine collection device, according to another example embodiment.

In FIGS. 9A-11C, the outlet 930, 1030 is at a location on the top wall 990A, 1090A spaced away from the distal end 934, 1034 of the collection member 912, 1012. However, as noted above, the outlet 930, 1030 can be at a distalmost point of the collection member 912, 1012 in other examples. FIG. 12 depicts a urine collection device 1200 including an outlet 1230 at a distalmost point of a collection member 1212. For example, the collection member 1212 can be formed from a plurality of sheets of material (e.g., the first sheet 942A, the second sheet 942B, and/or the third sheet 942C), and the outlet 1230 can include a port 1278 coupled to the distalmost point of the collection member 1212 at a seam 1299 between the sheets of material. In implementation, the port 1278 can be coupled to sheets of material by RF welding and/or RF heat sealing of the sheets around the port 1278. By locating the outlet 1230 at the distalmost point, pooling of urine in the collection member 1212 can be reduced (or minimized) relative to locating the outlet at more proximal locations.

Additionally, as shown in FIG. 12, because the port 1278 is at the distalmost point of the collection member 1212, the port 1278 can have a generally linear shape that can egress urine in a direction that is generally parallel to a longitudinal axis of the collection member 1212. Whereas, in FIGS. 9A-11C, the port 978, 1078 includes an approximately 90 degree bend to facilitate directing the urine through the top wall 990A, 1090A of the collection member 912, 1012 to the direction that is generally parallel to the longitudinal axis (and away from the user).

Figure 13:
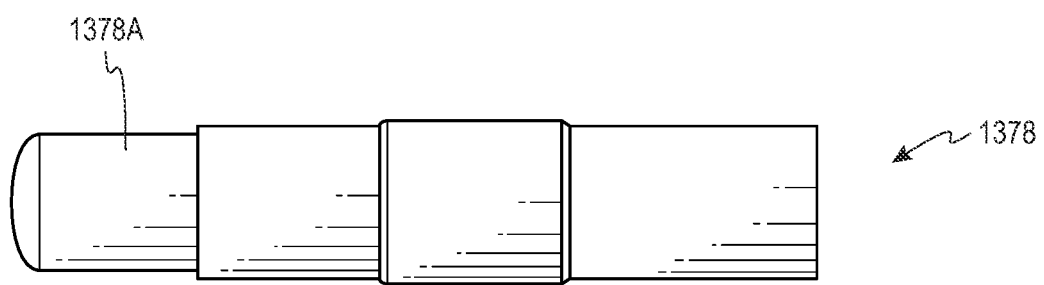
FIG. 13 illustrates a side view of a port, according to an example embodiment.

Additionally, as noted above, the port 978, 1078, 1278 of the urine collection device 900, 1000, 1200 can include a tapered end portion for coupling with the drain tube. For example, FIG. 13 depicts a port 1378 having a tapered end portion 1378A according to another example embodiment. Given that drain tubes may have different sizes (e.g., depending on the make and/or model of the vacuum device 256), the tapered end portion of the port 1378 can help to more universally couple the port 1378 to a plurality of differently sized drain tubes.

As described above, the urine collection device 900, 1000, 1200 forms the gaps 1197 between the first attachment member 996A, 1096A and the second attachment member 996B, 1096B when the urine collection device 900, 1000, 1200 is secured to the user. Additionally, as described above, the gaps 1197 can beneficially allow for air flow through the opening 936, 1036 and into the first chamber 938A, 1038A. This air flow can beneficially help to, for example, maintain sanitary conditions and/or improve user comfort. Additionally, for example, the airflow provided by the gaps can help to reduce (or minimize) a risk of a vacuum lock condition occurring.

However, in another example, the urine collection device 900, 1000, 1200 can include one or more baffle portions (i.e., flange portions) that reduce (or eliminate) a size of the gaps 1197 between the first attachment member 996A, 1096A and the second attachment member 996B, 1096B. As an example, FIG. 14 depicts a urine collection device 1400 that includes a first baffle portion 1499 extending between a first attachment member 1496A and the second attachment member 1496B on a first lateral side and a second baffle portion 1499 extending between the first attachment member 1496A and the second attachment member 1496B on a second lateral side. For user's with relatively small sized penises, the baffle portions 1499 can help to retain the user's penis in the urine collection device 1400 and/or reduce (or minimize) leakage of urine from a proximal end 1432. Within examples, the baffle portions 1499 can each have an accordion structure or a pleated structure that facilitates extending and retracting a size of the baffle portion 1499.

Figure 15A:
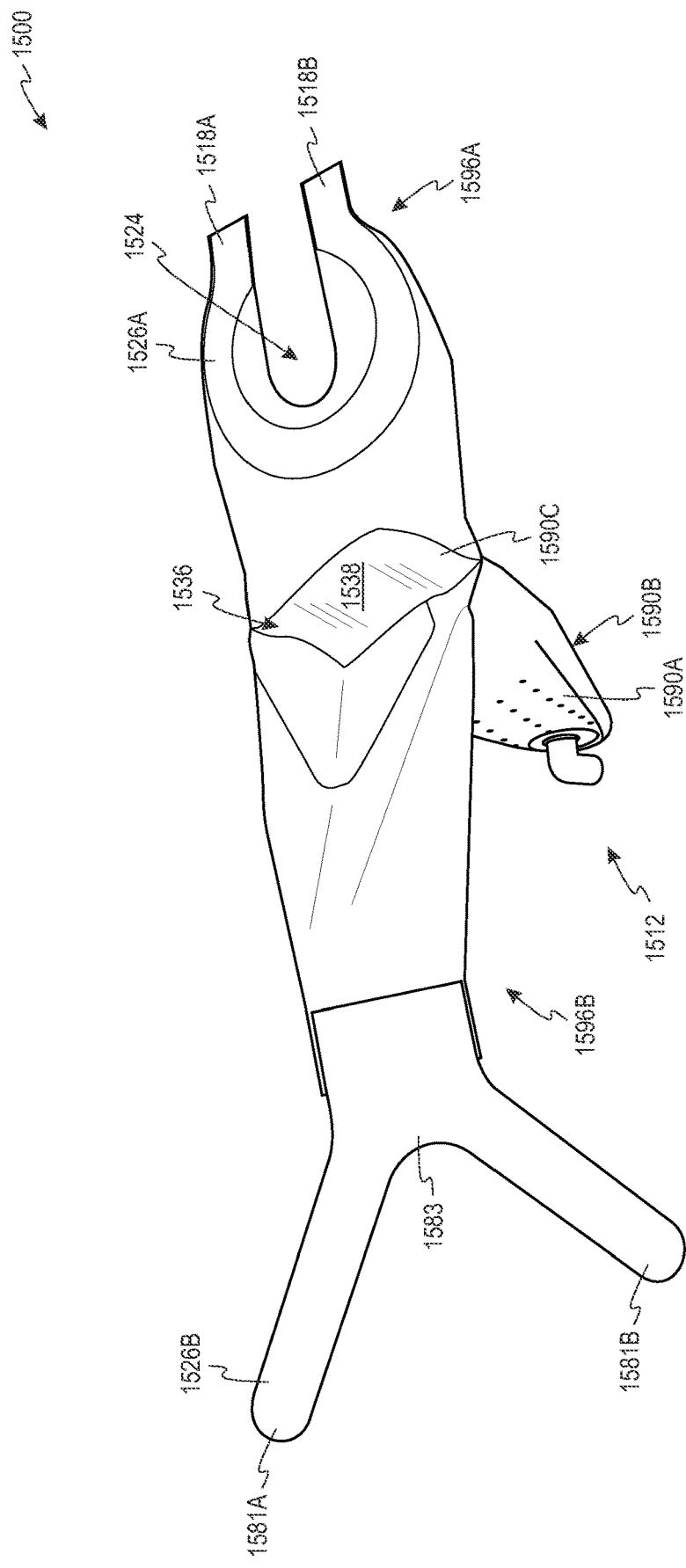
FIG. 15A illustrates a perspective view of a urine collection device, according to another example embodiment.
Figure 15B:
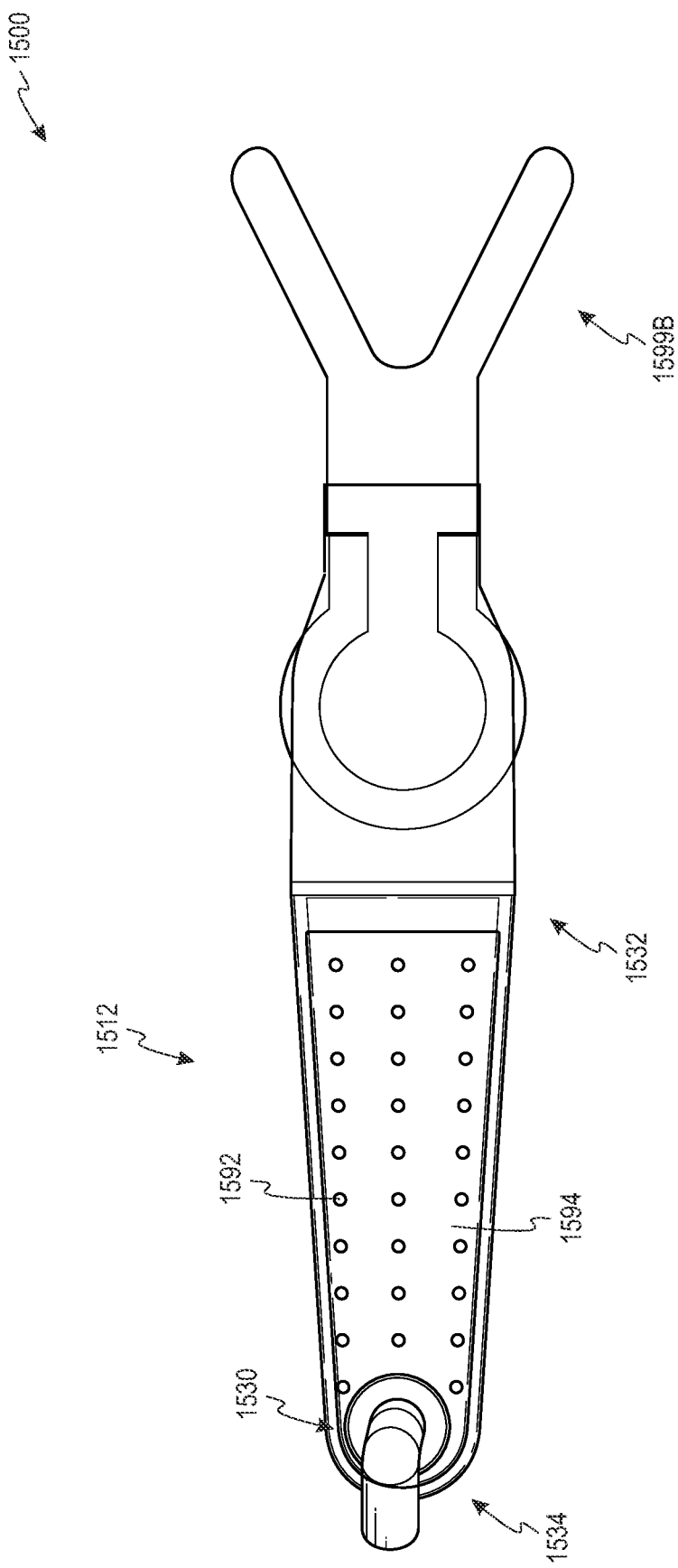
FIG. 15B illustrates a top view of the urine collection device shown in FIG. 15A, according to an example embodiment.

Referring now to FIGS. 15A-15B, a urine collection device 1500 is illustrated according to another example embodiment. The urine collection device 1500 is substantially similar to the urine collection devices 900, 1000, 1200, 1400 described above.

For example, as shown in FIGS. 15A-15B, the urine collection device 1500 includes a collection member 1512 extending from a proximal end 1532 to a distal end 1534. As shown in FIG. 15B, the collection member 1512 has a width that tapers inwardly along a longitudinal axis from the proximal end 1532 to the distal end 1534. As shown in FIG. 15A, the proximal end 1532 includes an opening 1536 that provides access to an internal cavity, which has a first chamber 1038A in communication with a second chamber 1038B (e.g., the internal cavity 938, 1038, which has the first chamber 938A, 1038A in fluid communication with the second chamber 938B, 1038B). The urine collection device 1500 includes an inner wall 1590C separating the first chamber from the second chamber and the inner wall includes a plurality of perforations 1592 through which the first chamber communicates with the second chamber. A spacer 1594 is in the second chamber. Additionally, the urine collection device 1500 includes an outlet 1530 for egressing urine from the internal cavity 1538 of the collection member 1512.

In FIGS. 15A-15B, a first attachment member 1596A extends from a bottom wall 1590B of the collection member 1512 at the proximal end 1532, and a second attachment member 1596B extends from a top wall 1590A of the collection member 1512 at the proximal end 1532. The first attachment member 1596A includes an inner side and an outer side opposite the inner side, and the second attachment member 1596B includes an outer side and an inner side. The first attachment member 1596A also includes a first adhesive 1526A on the outer side of the first attachment member 1596A, and the second attachment member 1596B includes a second adhesive 1526B on the inner side of the second attachment member 1596B to assist in securing the urine collection device 1500 to a user.

As shown in FIG. 15A, the first attachment member 1596A includes a first flexible member 1518A and a second flexible member 1518B. The first flexible member 1518A and the second flexible member 1518B of the first attachment member 1596A define an aperture 1524 in the first attachment member 1596A. As shown in FIG. 15A, the first flexible member 1518A and the second flexible member 1518B are separated and independently movable relative to each other (and/or the collection member 1512).

The urine collection device 1500 differs from the urine collection devices 900, 1000, 1200, 1400 in that the second attachment member 1596B includes a first arm 1581A and a second arm 1581B laterally extending from a center portion 1583. More specifically, the first arm 1581A and the second arm 1581B laterally diverge from each other as the first arm 1581A and the second arm 1581B extend proximally from the center portion 1583. In this arrangement, when the second attachment member 1596B is secured to the user, the center portion 1583 can be located at a middle area of the user's pelvic area and/or abdomen. Given that a relatively large portion of the male population has a greater density of hair near the middle area of the pelvic area and/or abdomen and a relatively lesser density of hair at areas adjacent to the middle area, the laterally-extending configuration of the second attachment member 1596B can reduce (or minimize) contact between the second adhesive 1526B and the user's hair. As such, the arrangement of the second attachment member 1596B and the second adhesive 1526B can improve patient comfort.

Additionally, because the first arm 1581A and the second arm 1581B laterally extend from the center portion 1583, the first arm 1581A and the second arm 1581B can help to increase stability of the urine collection device 1500 relative to urine collection devices that omit the first arm 1581A and the second arm 1581B laterally extending from the center portion 1583.

In FIGS. 15A-15B, the second attachment member 1596B is generally Y-shaped. As such, in FIGS. 15A-15B, the center portion 1583 can be a vertex from which the first arm 1581A and the second arm 1581B laterally and proximally extend. In another example, the first arm 1581A and the second arm 1581B can laterally extend from the center portion 1583 such that the second attachment member 1596B is generally T-shaped. Other examples are also possible.

Figure 16A:
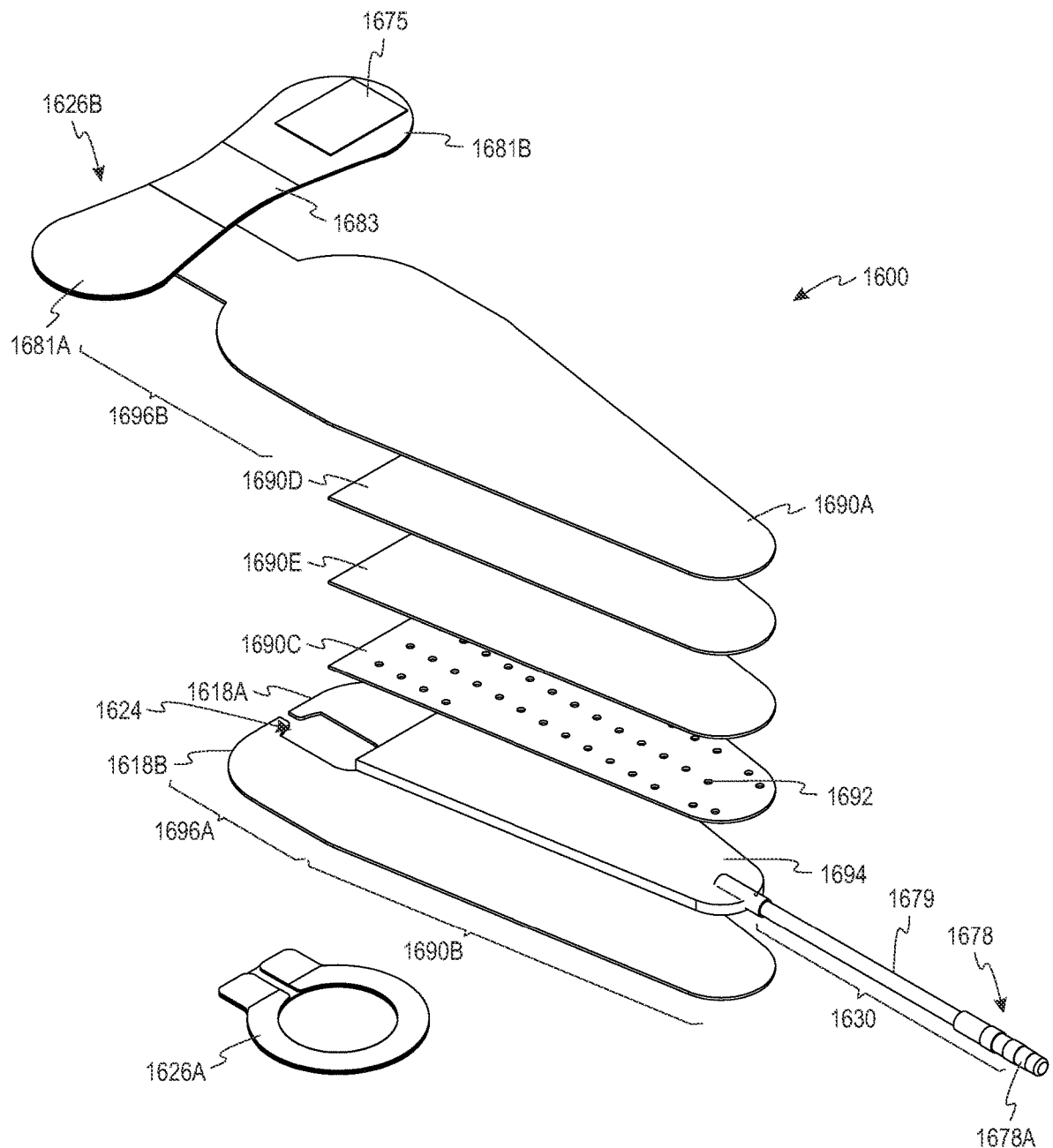
FIG. 16A illustrates an exploded view of a urine collection device, according to another example embodiment.
Figure 16B:
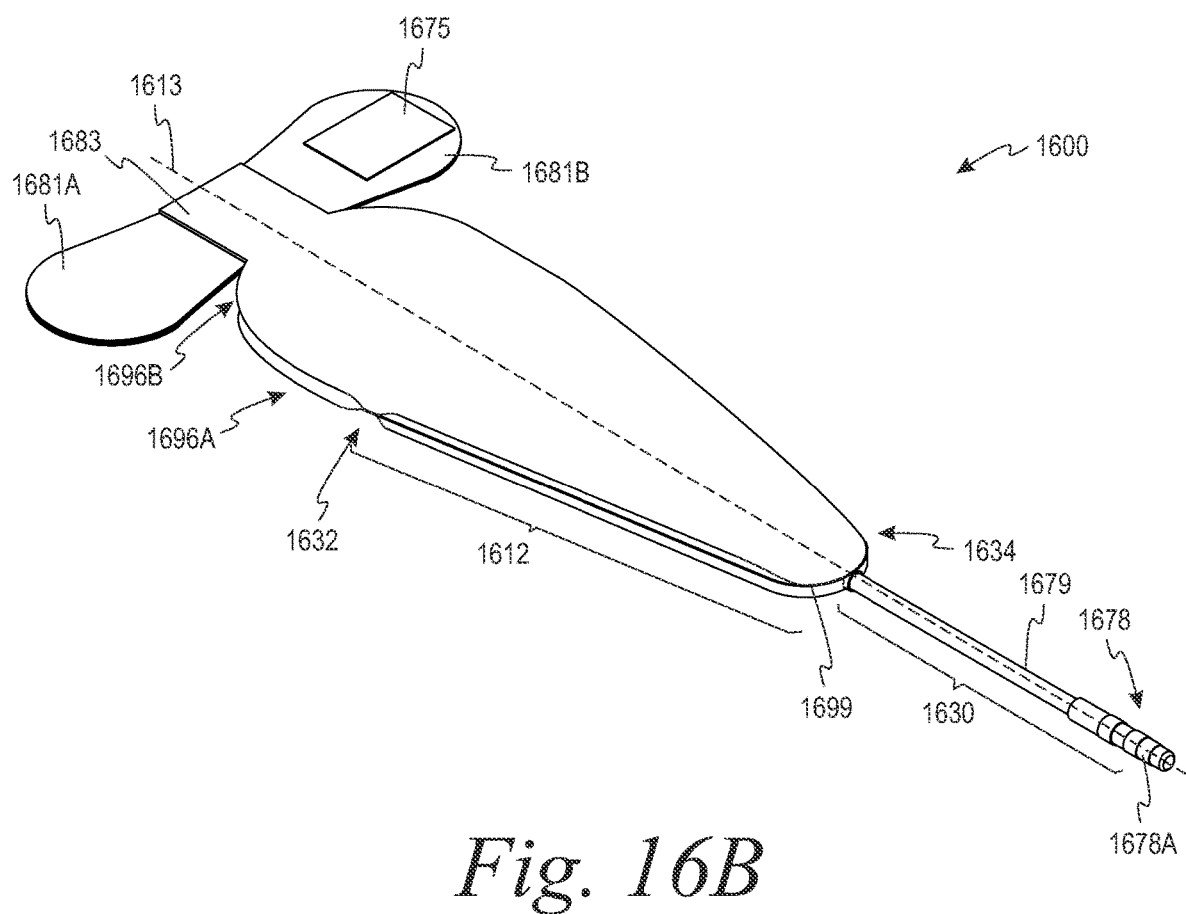
FIG. 16B illustrates a perspective view of the urine collection device shown in FIG. 16A, according to another example embodiment.
Figure 16C:
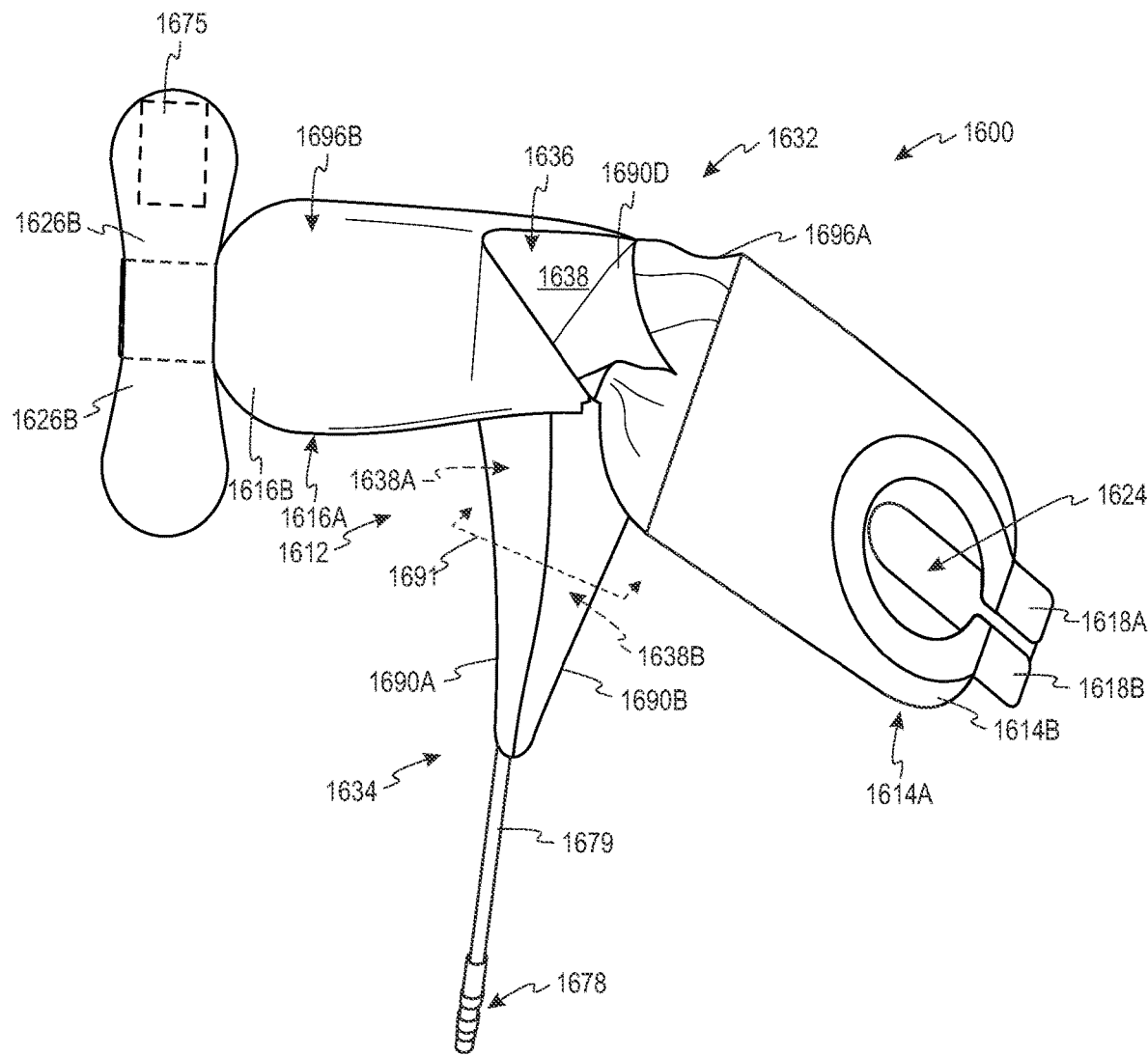
FIG. 16C illustrates another perspective view of the urine collection device shown in FIG. 16B, according to an example embodiment.
Figure 16D:
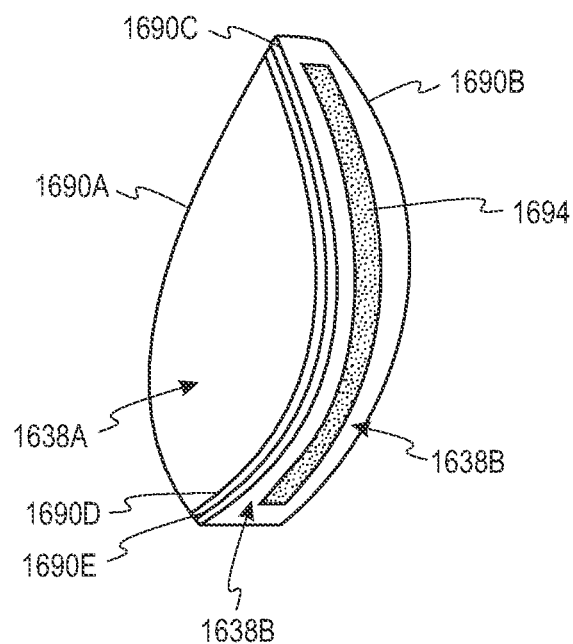
FIG. 16D illustrates a cross-sectional view of the urine collection device shown in FIG. 16C, according to an example embodiment.

Referring now to FIGS. 16A-16D, a urine collection device 1600 is illustrated according to another example embodiment. More specifically, FIG. 16A is an exploded view of the urine collection device 1600, FIG. 16B is a perspective view of the urine collection device 1600, FIG. 16C is another perspective view of the urine collection device 1600, and FIG. 16D depicts a cross-sectional view of the urine collection device 1600 taken through a line 1691 in FIG. 16C. The urine collection device 1600 is substantially similar to the urine collection devices 900, 1000, 1200, 1400, 1500 described above.

For example, as shown in FIGS. 16B-16C, the urine collection device 1600 includes a collection member 1612 extending from a proximal end 1632 to a distal end 1634. As shown in FIG. 16B, the collection member 1612 has a width that tapers inwardly along a longitudinal axis 1613 from the proximal end 1632 to the distal end 1634.

Additionally, in FIGS. 16A-16D, a first attachment member 1696A extends from a bottom wall 1690B of the collection member 1612 at the proximal end 1632, and a second attachment member 1696B extends from a top wall 1690A of the collection member 1612 at the proximal end 1632. The first attachment member 1696A includes an inner side 1614B and an outer side 1614A opposite the inner side 1614B, and the second attachment member 1696B includes an outer side 1616A and an inner side 1616B. The first attachment member 1696A also includes a first adhesive 1626A on the outer side 1614A of the first attachment member 1696A, and the second attachment member 1696B includes a second adhesive 1626B on the inner side 1616B of the second attachment member 1696B to assist in securing the urine collection device 1600 to a user.

FIGS. 16A and 16C depict the first attachment member 1696A including a first flexible member 1618A and a second flexible member 1618B. The first flexible member 1618A and the second flexible member 1618B of the first attachment member 1696A define an aperture 1624 in the first attachment member 1696A. As shown in FIG. 16A, the first flexible member 1618A and the second flexible member 1618B are separated and independently movable relative to each other (and/or the collection member 1612).

In FIGS. 16A-16C, the second adhesive 1626B includes a first arm 1681A and a second arm 1681B laterally extending from a center portion 1683. Specifically, the first arm 1681A and the second arm 1681B laterally extend from the center portion 1683 such that the second adhesive 1626B and the second attachment member 1696B form a generally T-shaped structure. In this arrangement, when the second attachment member 1696B is secured to the user via the adhesive 1626B, the center portion 1683 can be located at a middle area of the user's pelvic area and/or abdomen so that the first arm 1681A and the second arm 1681B extend to areas adjacent to the middle area of the user's pelvic area and/or abdomen. As noted above, this can help to reduce (or minimize) contact between the second adhesive 1626B and the user's hair, and/or improve stability of the urine collection device 1600 secured to the user.

In one implementation, a surface of the second adhesive 1626B which faces the user can have an active adhesive portion that is configured to adhere to the user. A portion of the second adhesive 1626B which faces the user can have an inactive adhesive portion that does not adhere to the user, such as the center portion 1683 between the first arm 1681A and the second arm 1681B. This can further assist in reducing (or minimizing) an extent to which the second adhesive 1626B adheres to the hair of the user at the middle area of the user's pelvic area and/or abdomen. In another implementation, the active adhesive portion of the second adhesive 1626B can include at least a portion (or an entirety) of the first arm 1681A, the second arm 1681B, and/or the center portion 1683 of the second adhesive 1626B, such that the second adhesive 1626B can adhere to the user at the first arm 1681A, the second arm 1681B, and/or the center portion 1683 of the second adhesive 1626B.

As shown in FIGS. 16C-16D, the proximal end 1632 of the collection member 1612 includes an opening 1636 that provides access to an internal cavity 1638, which has a first chamber 1638A in communication (i.e., fluid communication) with a second chamber 1638B. Like the urine collection devices 900, 1000, 1200, 1400, 1500 described above, the urine collection device 1600 includes an inner wall 1690C that separates the first chamber 1638A from the second chamber 1638B. The urine collection device 1600 includes an inner wall 1690C separating the first chamber 1638A from the second chamber 1638B and the inner wall 1690C includes a plurality of perforations 1692 through which the first chamber 1638A communicates with the second chamber 1638B.

Additionally, as shown in FIGS. 16A and 16D, the urine collection device 1600 includes, in the first chamber 1638A, a permeable layer 1690D and a wicking layer 1690E. The wicking layer 1690E is adjacent to the inner wall 1690C and the permeable layer 1690D is adjacent to the wicking layer 1690E (i.e., the wicking layer 1690E is between the permeable layer 1690D and the inner wall 1690C in the first chamber 1638A). In this arrangement, when a penis is inserted by a user through the opening 1636, the penis contacts the permeable layer 1690D in the first chamber 1638A while the wicking layer 1690E and the inner wall 1690C are below the permeable layer 1690D.

In general, the permeable layer 1690D can help to maintain the penis on a relatively dry surface, which in turn improves sanitary conditions, reduces the risk of infection, and/or improves user comfort. Within examples, the permeable layer 1690D can be made from a porous material, which may be hydrophilic or hydrophobic. As such, the permeable layer 1690D can direct urine received in the first chamber 1638A toward the second chamber 1638B. In one implementation, due to the hydrophobicity of the permeable layer 1690D, the permeable layer 1690D can repel urine and/or moisture in a direction away from the penis toward the wicking layer 1690E.

As one example, the permeable layer 1690D can be made from a polymer spunbond material. Additionally, in an example, the permeable layer 1690D can be formed by treating a material (e.g., a natural fiber material and/or a synthetic fiber material) with a surfactant, which lowers a surface tension of fluids (e.g., the urine and/or sweat) and forms a moisture transfer channel through the permeable layer 1690D to facilitate transferring the fluids or moisture from a side of the permeable layer 1690D that engages the penis (e.g., in the first chamber 1638A) to a side of the permeable layer 1690D that faces the wicking layer 1690E (i.e., in a direction from the top wall 1690A toward the bottom wall 1690B).

The wicking layer 1690E can assist in pulling the urine, moisture, or sweat through the permeable layer 1690D toward the inner wall 1690C and the second chamber 1638B. For example, the wicking layer 1690E can be made from a material that is configured to provide for capillary action to move the urine, moisture, or sweat from a side of the wicking layer 1690E facing the permeable layer 1690D to a side of the wicking layer 1690E facing the inner wall 1690C (i.e., in the direction from the top wall 1690A toward the bottom wall 1690B). In particular, for example, the wicking layer 1690E can be configured to provide for transverse wicking of the urine, moisture, and/or sweat from the permeable layer 1690D to the inner wall 1690C (and, thus, the second chamber 1638B). As one example, the wicking layer 1690E can be made from a mechanically absorbent polyester mesh material.

As shown in FIGS. 16A and 16D, a spacer 1694 is in the second chamber 1638B. Additionally, the urine collection device 1600 includes an outlet 1630 for egressing urine from the internal cavity 1638 of the collection member 1612. As described above, the spacer 1694 can, for example, help to separate the bottom wall 1690B from the inner wall 1690C. This can help to inhibit (or prevent) an occlusion of the second chamber 1638B, which may negatively impact egress of the urine from the urine collection device 1600. Additionally, for example, the spacer 1694 can help to inhibit (or prevent) an occurrence of a vacuum lock condition due to the vacuum pressure applied by a vacuum device (such as, e.g., the vacuum device 256 depicted in FIG. 2).

As shown in FIGS. 16A-16B, the outlet 1630 can include a port 1678 coupled to the spacer 1694 by a tube 1679 extending through a seam 1699 at the distal end 1634 of the collection member 1612 (e.g., at a distalmost point of the collection member 1612). Additionally, the port 1678 can include a tapered end portion 1678A, which can help to more universally couple the port 1678 to a plurality of differently sized drain tubes.

The tube 1679 can assist in spacing a point of connection between the urine collection device 1600 and a drain tube farther away from the patient. This can help to improve handling by medical practitioners as the tube 1679 can provide for greater flexibility and range of movement of the port 1678 while coupling the port 1678 to the drain tube and/or decoupling the port 1678 from the drain tube. Additionally, the tube 1679 can help to reduce a risk that a medical practitioner will inadvertently decouple the urine collection device 1600 from the user when the medical practitioner manipulates the location and/or orientation of the port 1678 to couple the port 1678 with the drain tube.

As shown in FIG. 16, the tube 1679 can extend within the spacer 1694. This can help to reduce (or prevent) a risk of occlusion due to vacuum suction and adhesion of the inner wall 1690C and the bottom wall 1690B. As an example, the tube 1679 can be coupled to the spacer 1694 by bonding via solvents, adhesives, welding, and/or snap-fit.

In this arrangement, the urine can be initially received in the first chamber 1638A of the internal cavity 1638. The urine may initially contact the permeable layer 1690D, which supports the penis in the first chamber 1638A. The urine can pass through the permeable layer 1690D to the wicking layer 1690E, which can provide capillary action to move the urine from the permeable layer 1690D to the inner wall 1690C. The urine can then pass through the perforations 1692 in the inner wall 1690C to the second chamber 1638B. In the second chamber 1638B, the urine can flow distally and egress from the collection member 1612 at the outlet 1630. As described above, this flow of the urine through the collection member 1612 can be assisted by the hydrophobicity of the permeable layer 1690D, the capillary action of the wicking layer 1690E, gravity, and/or a vacuum pressure applied by a vacuum device (e.g., the vacuum device 256) at the outlet 1630 of the collection member 1612.

Additionally, as shown in FIGS. 16A-16D, the urine collection device 1600 can include a label 1675. The label 1675 can provide for recording operation information (e.g., a time of securement of the urine collection device 1600 to the patient), which can help medical personnel more readily identify information related to patient care. In FIGS. 16A-16C, the label 1675 is on the second arm 1681B, which can provide for easy access on an outer side of the urine collection device 1600 when the urine collection device 1600 is secured to a user. However, the label 1675 can be at additional or alternative locations on the urine collection device 1600 in other examples.

As described above, the collection members are suitable to direct urine to an outlet of the collection member, and the outlet is suitable to egress the urine from the collection member. In some examples, however, the collection member can be configured to retain a volume of urine in instances in which a drain tube is occluded and/or closed (e.g., by a valve). In one implementation, the collection member can be suitable to contain at least approximately 400 milliliters (ml) of urine.

Additionally, as described above, the urine collection device 900, 1000, 1200, 1400, 1500, 1600 can include an inner wall 990C, 1090C, 1290C, 1490C, 1590C, 1690C that includes a plurality of perforations 992, 1092, 1292, 1492, 1592, 1692. In the examples shown in FIGS. 9A-12 and 14-16D, the perforations 992, 1092, 1292, 1492, 1592, 1692 are all approximately the same size as each other. However, in another example, the perforations 992, 1092, 1292, 1492, 1592, 1692 can have different sizes.

Figure 17:
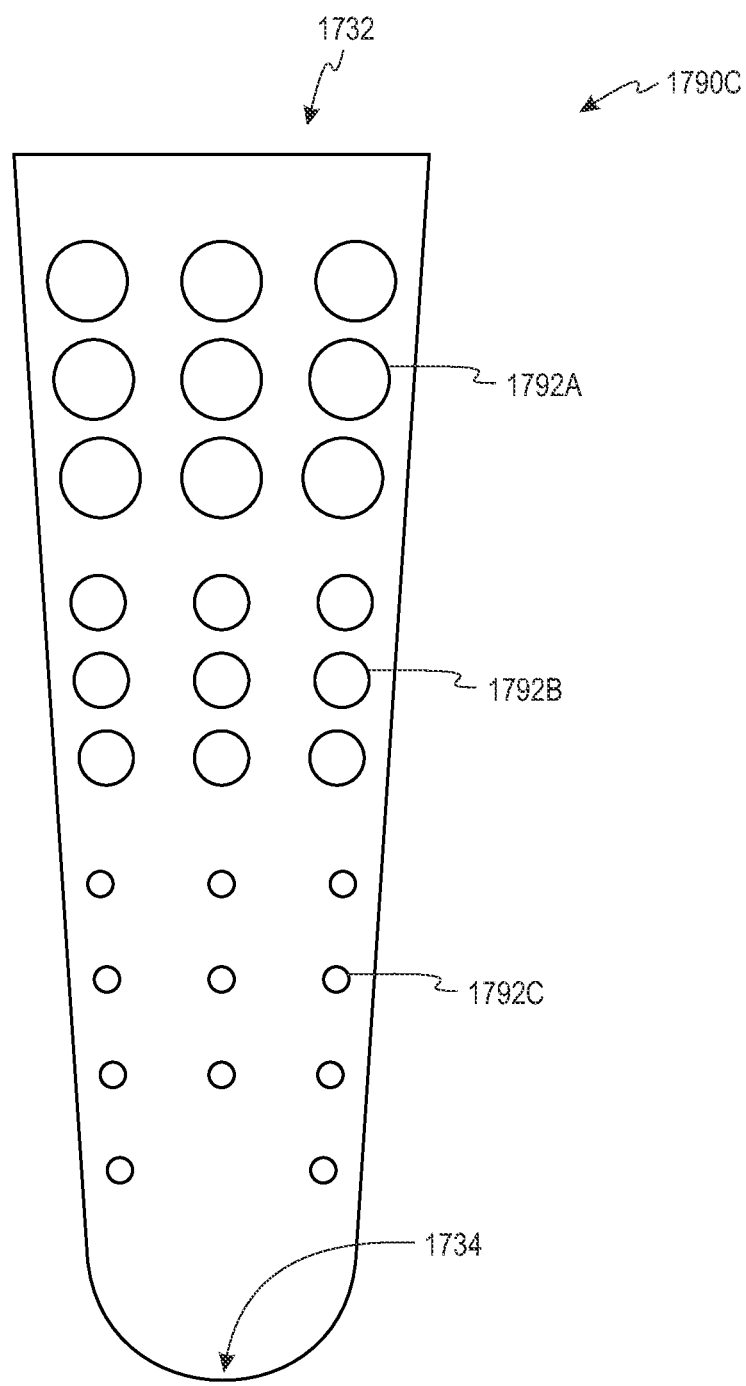
FIG. 17 illustrates an inner wall of a urine collection device, according to an example embodiment.

As one example, FIG. 17 depicts an inner wall 1790C having a plurality of perforations 1792A-1792C of a plurality of different sizes and which can be used with any of the urine collection devices 900, 1000, 1200, 1400, 1500, 1600 described herein. In FIG. 17, the perforations 1792A-1792C include a plurality of first perforations 1792A each having a first size, a plurality of second perforations 1792B each having a second size, and a plurality of third perforations 1792C each having a third size. The first perforations 1792A are proximal of the second perforations 1792B, which are proximal of the third perforations 1792C. In this example, the first size of the first perforations 1792A is larger than the second size of the second perforations 1792B, which is larger than the third size of the third perforations 1792C.

Thus, in FIG. 17, the perforations 1792A-1792C decrease in size along a direction from the proximal end 1732 to a distal end 1734. This can help to improve suction when the urine collection device 900, 1000, 1200, 1400, 1500, 1600 is used with a vacuum device (e.g., the vacuum device 256) and/or more rapidly transfer urine from the first chamber 938A, 1038A, 1638A to the second chamber 938B, 1038B, 1638B.

In FIG. 17, the perforations 1792A-1792C include three different sizes. However, in another example, the perforations 1792A-1792C can include two different sizes or more than three different sizes. For instance, in one implementation, the perforations 1792A-1792C can continuously and progressively decrease in size along the direction from the proximal end 1732 to the distal end 1734. Additionally, in other examples, the perforations 1792A-1792C can increase in size along the direction from the proximal end 1732 to the distal end 1734 (i.e., the first perforations 1792A can be smaller than the second perforations 1792B and the second perforations 1792B can be smaller than the third perforations 1792C). In yet another example, the perforations 1792A-1792C can be arranged such that relatively large sized perforations 1792A are intermixed with relatively small size perforations 1792B, 1792C along the direction from the proximal end 1732 to the distal end 1734.

In examples described above, the inner wall 990C, 1090C, 1290C, 1490C, 1590C, 1690C, 1790C can be made from a liquid impermeable material (e.g., a plastic material) such that the urine can flow from the first chamber 938A, 1038A, 1638A to the second chamber 938B, 1038B, 1638B through the perforations 992, 1092, 1292, 1492, 1592, 1692, 1792A-1792C. In such examples, the perforations 992, 1092, 1292, 1492, 1592, 1692, 1792A-1792C can thus define fluid passageways through the inner wall 990C from the first chamber 938A, 1038A, 1638A to the second chamber 938B, 1038B, 1638B.

In another example, the inner wall 990C, 1090C, 1290C, 1490C, 1590C, 1690C, 1790C can be combined with the permeable layer 1690D to define such fluid passageways from the first chamber 938A, 1038A, 1638A to the second chamber 938B, 1038B, 1638B. For instance, the permeable layer 1690D can be configured to have (i) a first zone that inhibits the transfer of urine from a side of the permeable layer 1690D that faces the first chamber 1638A to a side of the permeable layer 1690D that faces the second chamber 1638B, and (ii) and a second zone that allows the transfer of urine from the side of the permeable layer 1690D that faces the first chamber 1638A to the side of the permeable layer 1690D that faces the second chamber 1638B. In one implementation, the first zone and the second zones can be formed by applying a surface treatment (e.g., a coating) to the permeable layer 1690D at the first zone, but not the second zones. The surface treatment can include, for instance, a hydrophobic coating and/or a liquid repellant coating (e.g., a fluoropolymer).

Figures 18A, 18B:
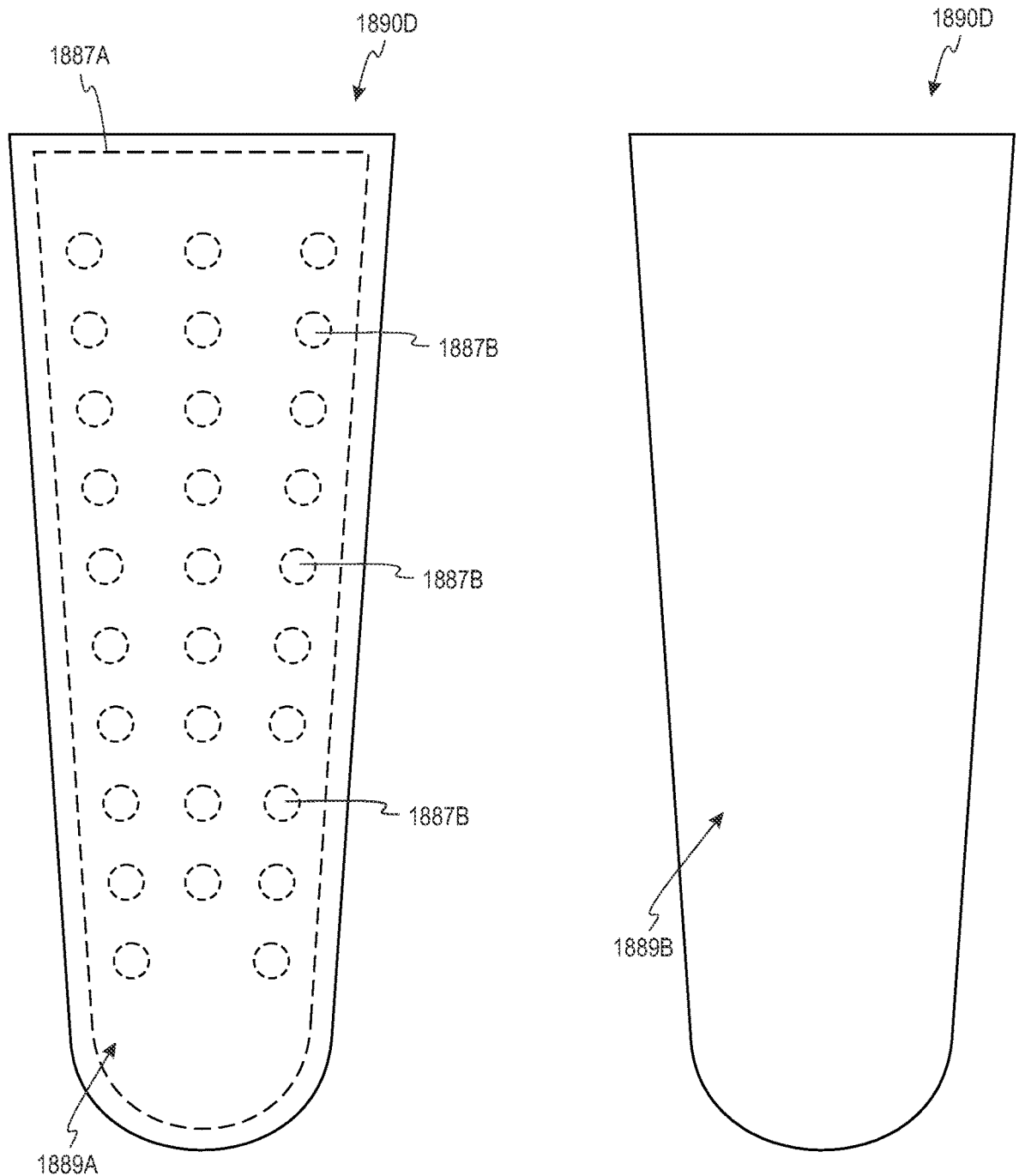
FIG. 18A illustrates a first side of a permeable layer of a urine collection device, according to an example embodiment.
FIG. 18B illustrates a second side of the permeable layer shown in FIG. 18A, according to an example embodiment.

The first zone and the second zones can be arranged in a pattern on the permeable layer 1690D in manner similar to the patterns illustrated and described for the perforations 992, 1092, 1292, 1492, 1592, 1692, 1792A-1792C on the inner walls 990C, 1090C, 1290C, 1490C, 1590C, 1690C, 1790C. As one example, FIGS. 18A-18B depict a permeable layer 1890D that includes a first zone 1887A and a plurality of second zones 1887B. In particular, FIG. 18A depicts a side 1889A of the permeable layer 1890D that can face the first chamber 938A, 1038A, 1638A of the urine collection devices device 900, 1000, 1200, 1400, 1500, 1600 and FIG. 18B depicts a side 1889B of the permeable layer 1890D that can face the second chamber 938B, 1038B, 1638B of the urine collection devices device 900, 1000, 1200, 1400, 1500, 1600. As described above, the first zone 1887A can include the surface treatment that inhibits the transfer of the urine from the first side 1889A of the permeable layer 1890D facing the first chamber to the second side 1889B of the permeable layer 1890D facing the second chamber.

Also, as described above, the second zones 1887B omit the surface treatment. In this arrangement, when the urine contacts the side 1889A facing the first chamber, the urine will flow over and around the first zone 1887A to the second zones 1887B and, at the second zones 1887B, the urine will transfer through the permeable layer 1890D from the first side 1889A facing the first chamber to the second side 1889B facing the second chamber.

Figure 19A:
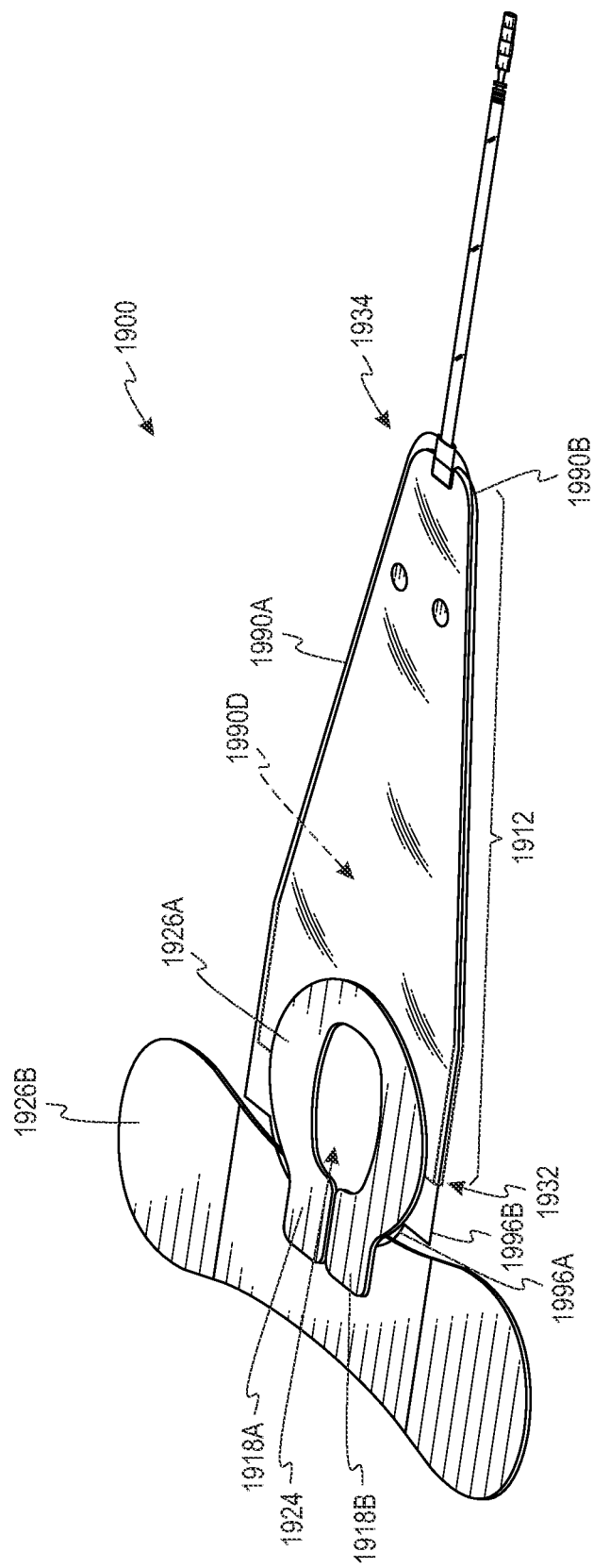
FIG. 19A illustrates a perspective view of a urine collection device, according to another example embodiment.
Figure 19B:
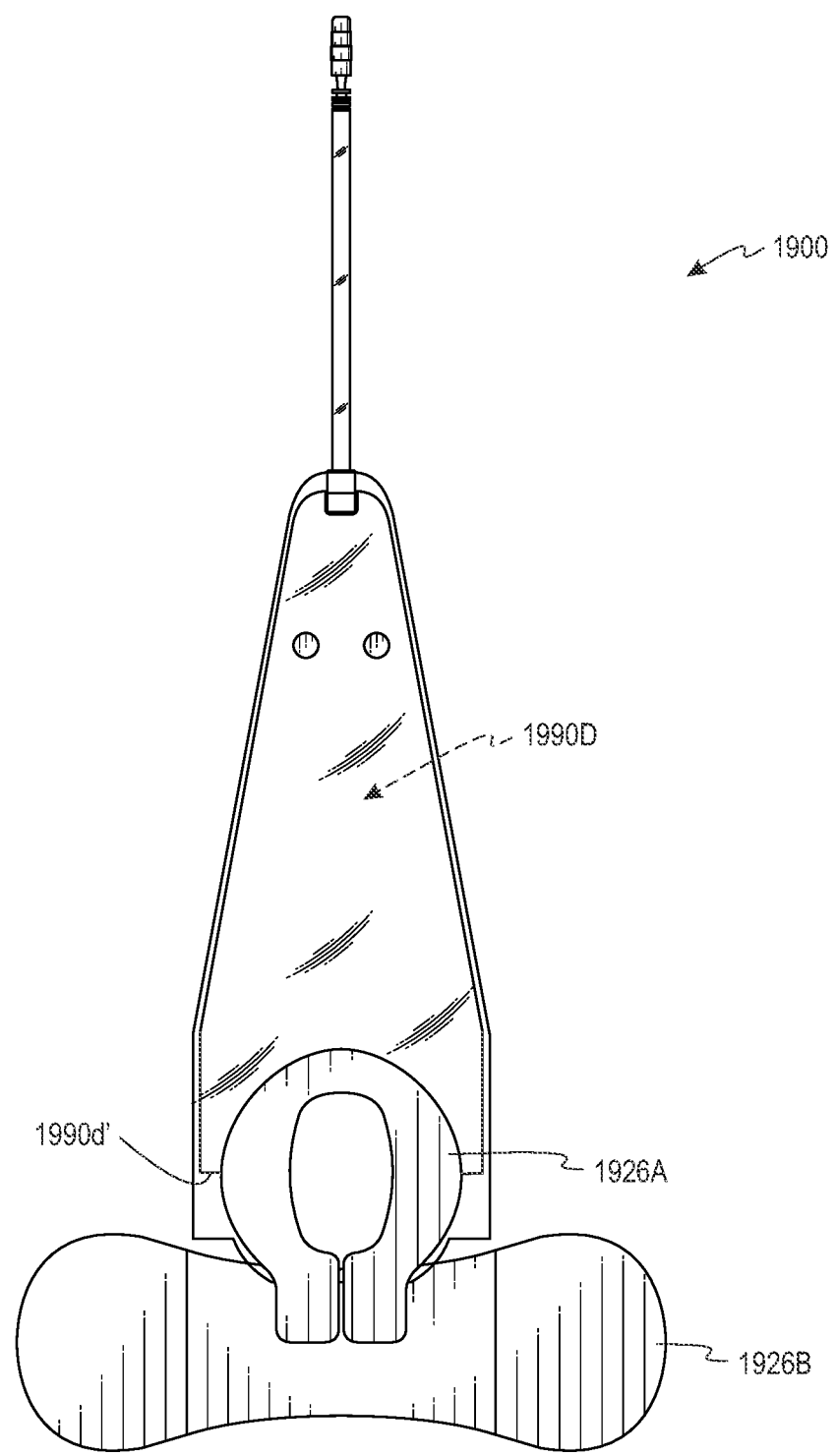
FIG. 19B illustrates a top plan view of the urine collection device shown in FIG. 19A, according to an example embodiment.
Figure 19C:
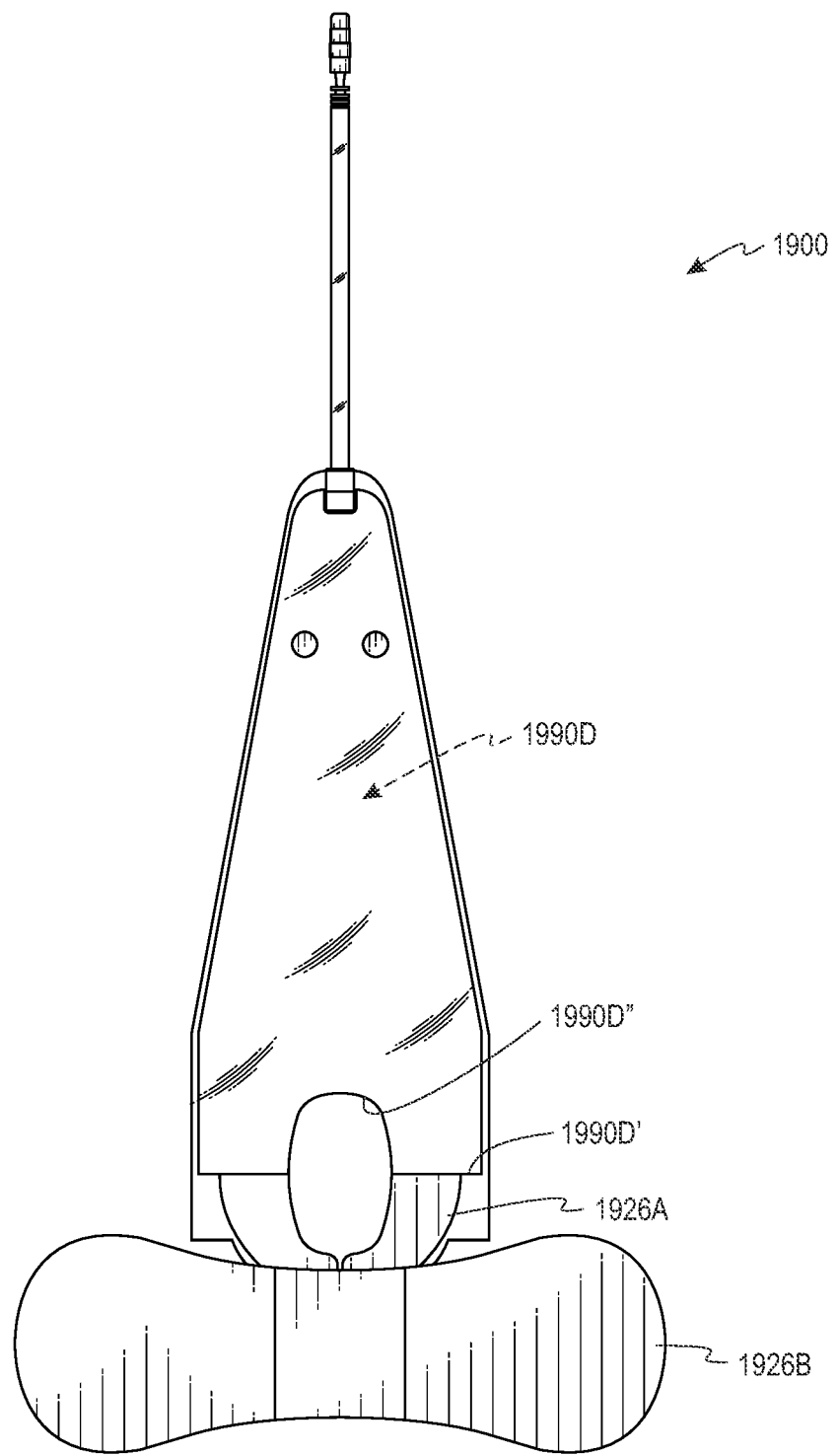
FIG. 19C illustrates a bottom plan view of the urine collection device shown in FIG. 19A, according to an example embodiment.
Figure 19D:
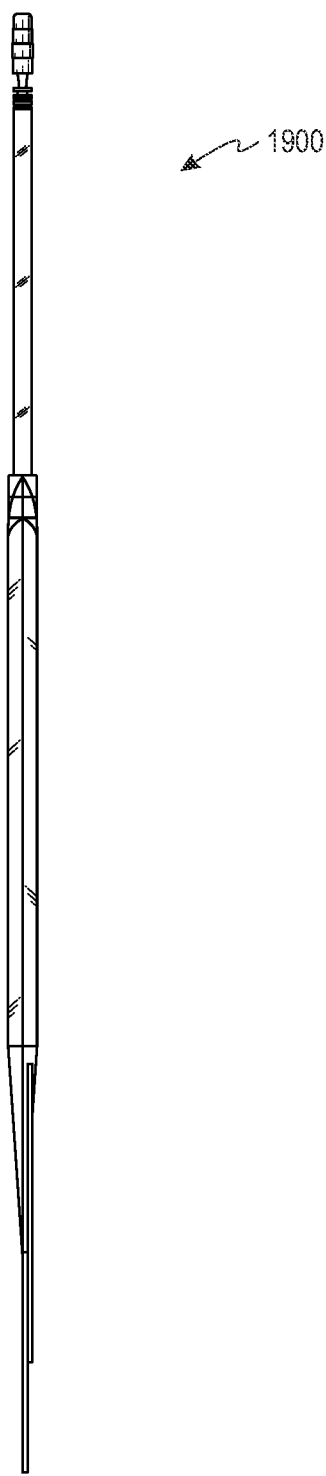
FIG. 19D illustrates a first side elevation view of the urine collection device shown in FIG. 19A, according to an example embodiment.
Figure 19E:
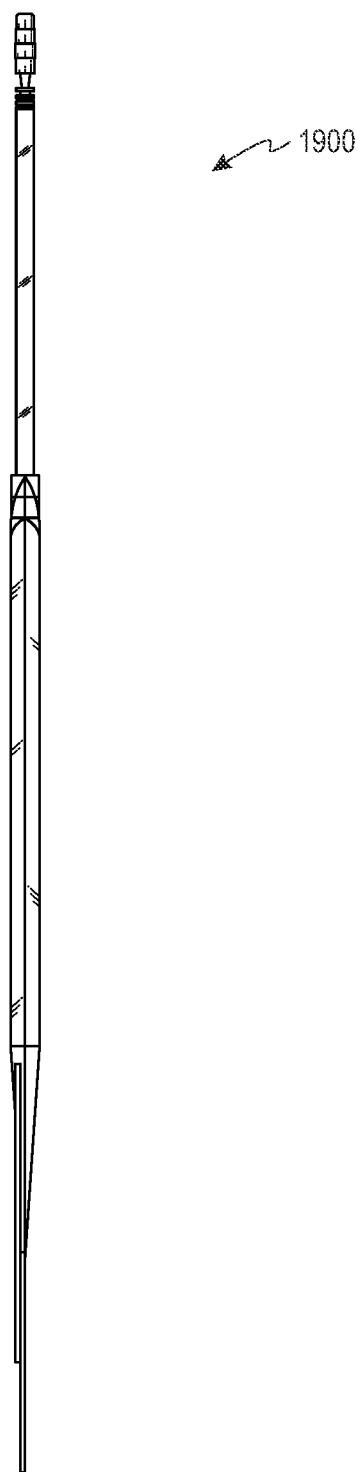
FIG. 19E illustrates a second side elevation view of the urine collection device shown in FIG. 19A, according to an example embodiment.
Figure 19F:
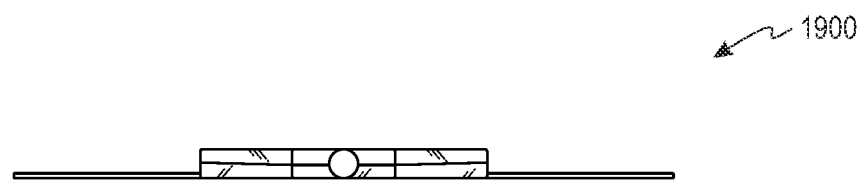
FIG. 19F illustrates a third side elevation view of the urine collection device shown in FIG. 19A, according to an example embodiment.
Figure 19G:
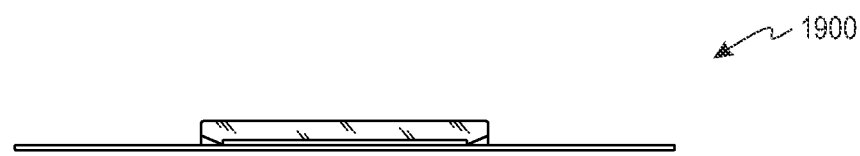
FIG. 19G illustrates a fourth side elevation view of the urine collection device shown in FIG. 19A, according to an example embodiment.

Referring now to FIGS. 19A-19E, a urine collection device 1900 is depicted according to another example embodiment. FIG. 19A depicts a perspective view of the urine collection device 1900, FIG. 19B depicts a top view of the urine collection device 1900, FIG. 19C depicts a bottom view of the urine collection device 1900, FIG. 19D depicts a first side view of the urine collection device 1900, FIG. 19E depicts a second side view of the urine collection device, FIG. 19F depicts a third side view of the urine collection device, and FIG. 19G depicts a fourth side view of the urine collection device. The urine collection device 1900 is substantially similar to the urine collection devices 900, 1000, 1200, 1400, 1500, 1600 described above.

For example, the urine collection device 1900 includes a collection member 1912 extending from a proximal end 1932 to a distal end 1934. A first attachment member 1996A extends from a bottom wall 1990B of the collection member 1912 at the proximal end 1932, and a second attachment member 1996B extends from a top wall 1990A of the collection member 1612 at the proximal end 1932. The first attachment member 1996A also includes a first adhesive 1926A, and the second attachment member 1996B includes a second adhesive 1926B to assist in securing the urine collection device 1900 to a user as described above.

The first attachment member 1996A includes a first flexible member 1918A and a second flexible member 1918B. The first flexible member 1918A and the second flexible member 1918B of the first attachment member 1996A define an aperture 1924 in the first attachment member 1996A. In FIGS. 19A-19C, the first attachment member 1996A and/or the first adhesive 1926A define a shape of the aperture 1924. For instance, in FIGS. 19A-19C, the first attachment member 1996A and/or the first adhesive 1926A define a generally oblong and/or a substantially elliptical shape of the aperture 1924. Within examples, the generally oblong and/or a substantially elliptical shape of aperture 1924 can assist in improving securing the first attachment member 1996A to the user in relatively close proximity to the penis of the user.

Additionally, the urine collection device 1900 includes an inner wall (not shown), a permeable layer 1990D, and/or a wicking layer (not shown) between a first chamber (not shown) and a second chamber (not shown) as described above with respect to FIGS. 16A-16D. However, the permeable layer 1990D in FIGS. 19A-19C extends more proximally than the permeable layer 1690D in FIGS. 16A-16D. Specifically, in FIGS. 19A-19C, the permeable layer 1990D can be arranged in the urine collection device 1900 such that a proximal-most portion 1990D' of the permeable layer 1990D overlaps with a portion of the first adhesive 1926A. For instance, as shown in FIG. 19C, the proximal-most portion 1990D' of the permeable layer 1990D can include a notch 1990D" having a shape that corresponds to a shape of an inner edge of the first adhesive 1926A. By arranging the permeable layer 1990D with the proximal-most portion 1990D' overlapping with a portion of the first adhesive 1926A, the permeable layer 1990D can assist in mitigating (or preventing) leakage of urine from the urine collection device 1900 when a user is turned (e.g., relative to a hospital bed).

Figure 20:
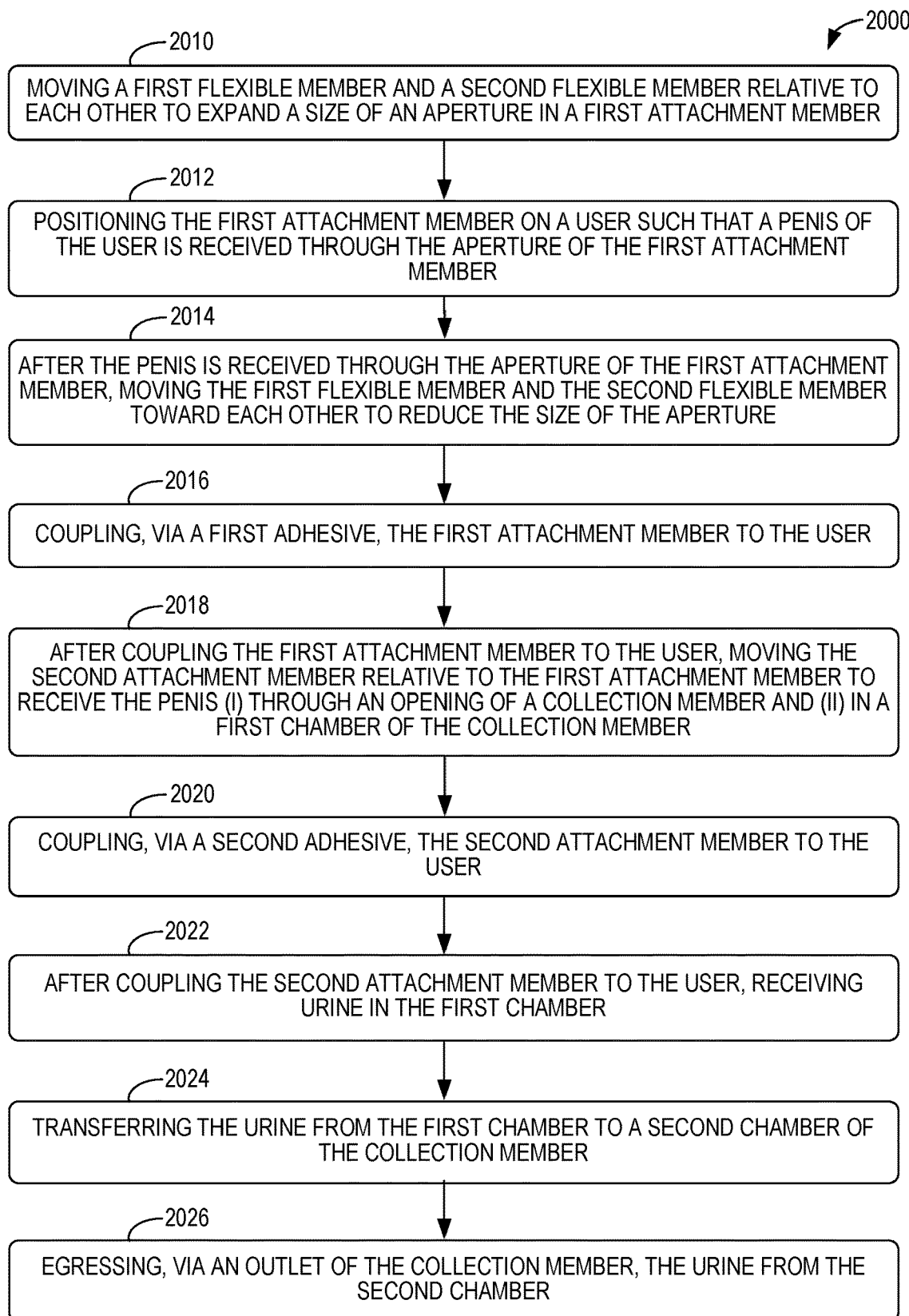
FIG. 20 illustrates a flowchart for a process for collecting urine, according to an example embodiment.

Referring now to FIG. 20, a flowchart for a process 2000 for collecting urine is illustrated according to an example embodiment. As shown in FIG. 20, at block 2010, the process 2000 includes moving a first flexible member and a second flexible member relative to each other to expand a size of an aperture in the first attachment member. At block 2012, the process 2000 includes positioning the first attachment member on a user such that a penis of the user is received through the aperture. After the penis is received through the aperture of the first attachment member at block 2012, the process 2000 includes moving the first flexible member and the second flexible member toward each other to reduce the size of the aperture at block 2014. At block 2016, the process 2000 includes coupling, via a first adhesive, the first attachment member to the user. After coupling the first attachment member to the user at block 2016, the process 2000 includes moving the second attachment member relative to the first attachment member to receive the penis (i) through an opening of a collection member and (ii) in a first chamber of the collection member at block 2018. At block 2020, the process 2000 can include coupling, via a second adhesive, the second attachment member to the user.

After coupling the second attachment member to the user at block 2020, the process 2000 can include receiving urine in the first chamber at block 2022. At block 2024, the process 2000 can include transferring the urine from the first chamber to a second chamber of the collection member. At block 2026, the process 2000 can include egressing, via an outlet of the collection member, the urine from the second chamber.

Figure 21:
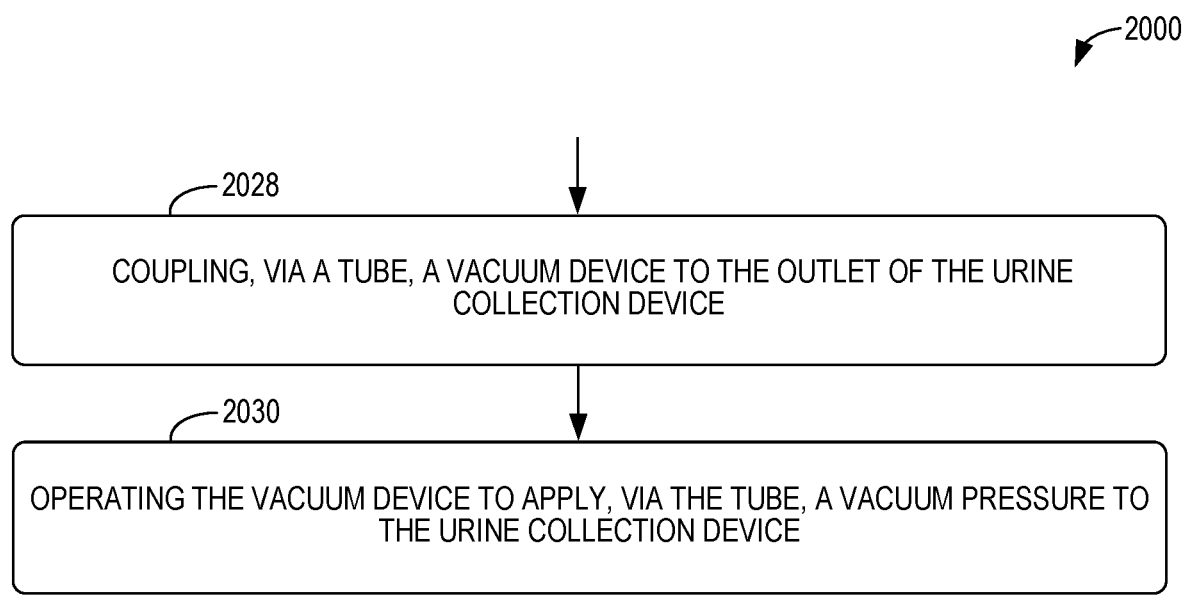
FIG. 21 illustrates a flowchart for a process for collecting urine that can be performed with the process shown in FIG. 20, according to an example embodiment.

FIG. 21 depicts additional aspects of the process 2000 according to further examples. As shown in FIG. 21, the process 2000 can also include coupling, via a tube, a vacuum device to the outlet of the urine collection device at block 2028. At block 2030, the process 2030 can include operating the vacuum device to apply, via the tube, a vacuum pressure to the urine collection device.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A urine collection device, comprising:
a collection member extending from a proximal end to a distal end, wherein the collection member has a longitudinal axis that extends between the proximal end and the distal end, wherein the proximal end comprises an opening that provides access to an internal cavity of the collection member, wherein the internal cavity comprises a first chamber extending from the proximal end to the distal end, and wherein the first chamber is in fluid communication with a second chamber extending from the proximal end to the distal end;
a spacer in the second chamber;
a first attachment member extending from a bottom wall of the collection member at the proximal end, wherein the first attachment member defines an aperture;
a second attachment member extending from a top wall of the collection member at the proximal end; and
an outlet for egres sing urine from the internal cavity of the collection member,
wherein the collection member is suitable to (i) direct urine from the first chamber to the second chamber and (ii) direct the urine in the second chamber distally toward the outlet,
wherein the opening at the proximal end of the collection member has a center axis that is transverse to a center axis of the aperture defined by the first attachment member.

2. The urine collection device of claim 1, wherein the first attachment member comprises a first flexible member and a second flexible member that are movable relative to each other to facilitate access to the aperture in the first attachment member.

3. The urine collection device of claim 2, wherein the first flexible member is separated from the second flexible member by a slit extending proximally from the aperture in the first attachment member.

4. The urine collection device of claim 1, wherein the first attachment member comprises a first adhesive to assist in securing the first attachment member to a user, and wherein the second attachment member comprises a second adhesive to assist in securing the second attachment member to the user.

5. The urine collection device of claim 4, wherein the first adhesive is coupled to an outer side of the first attachment member, and wherein the second adhesive is coupled to an inner side of the second attachment member.

6. The urine collection device of claim 4, wherein the first adhesive extends entirely around the aperture in the first attachment member.

7. The urine collection device of claim 1, further comprising a wicking layer separating the first chamber and the second chamber,
wherein the wicking layer is configured to move the urine from the first chamber toward the second chamber.

8. The urine collection device of claim 7, wherein the wicking layer comprises a mechanically absorbent polyester mesh material.

9. The urine collection device of claim 7, further comprising a permeable layer adjacent to the wicking layer, wherein the opening in the collection member is defined by the permeable layer and the top wall of the collection member.

10. The urine collection device of claim 9, wherein the permeable layer and the wicking layer inhibit access to the second chamber from outside of the first chamber.

11. The urine collection device of claim 10, wherein a proximal-most portion of the permeable layer overlaps with a portion of a first adhesive on the first attachment member.

12. The urine collection device of claim 11, wherein the permeable layer comprises a notch having a shape that corresponds to a shape of an inner edge of a first adhesive coupled to the first attachment member.

13. The urine collection device of claim 1, wherein the outlet comprises a tube and a port coupled to the tube, wherein the port is configured to couple to a drain tube of a vacuum device.

14. The urine collection device of claim 13, wherein the outlet is at a distalmost point of the collection member.

15. The urine collection device of claim 14, wherein the collection member comprises a first sheet of material coupled to a second sheet of material, and wherein the port is coupled to the distalmost point of the collection member at a seam between the first sheet of material and the second sheet of material.

16. The urine collection device of claim 1, wherein the spacer is an open-cell foam material configured to allow the urine to flow through the spacer in a direction from the proximal end to the distal end.

17. The urine collection device of claim 1, wherein the spacer is configured to inhibit a vacuum lock condition.

18. The urine collection device of claim 1, wherein the second attachment member is T-shaped.

19. The urine collection device of claim 1, wherein the center axis of the opening at the proximal end of the collection member is orthogonal to the center axis of the aperture defined by the first attachment member when the first attachment member and the second attachment member extend parallel to the longitudinal axis.

20. The urine collection device of claim 1, wherein the opening is distal of the aperture.

* * * * *

UNITED STATES PATENT AND TRADEMARK OFFICE
CERTIFICATE OF CORRECTION

| | | |
|---|---|---|
| PATENT NO. | : 11,779,485 B2 | Page 1 of 1 |
| APPLICATION NO. | : 17/986051 | |
| DATED | : October 10, 2023 | |
| INVENTOR(S) | : Brian J. Ecklund et al. | |

It is certified that error appears in the above-identified patent and that said Letters Patent is hereby corrected as shown below:

On the Title Page

On page 2, item (60) should correctly appear as follows:
Provisional application No. 62/770,734, filed on Nov. 21, 2018, provisional application No. 62/735,686, filed on Sep. 24, 2018, provisional application No. 62/630,561, filed on Feb. 14, 2018

Signed and Sealed this
Twenty-ninth Day of April, 2025

Coke Morgan Stewart
*Acting Director of the United States Patent and Trademark Office*